US 9,536,201 B2

(12) United States Patent
Reshef et al.

(10) Patent No.: US 9,536,201 B2
(45) Date of Patent: Jan. 3, 2017

(54) IDENTIFYING ASSOCIATIONS IN DATA AND PERFORMING DATA ANALYSIS USING A NORMALIZED HIGHEST MUTUAL INFORMATION SCORE

(71) Applicants: David N. Reshef, Boston, MA (US); Yakir A. Reshef, Cambridge, MA (US)

(72) Inventors: David N. Reshef, Boston, MA (US); Yakir A. Reshef, Cambridge, MA (US)

( * ) Notice: Subject to any disclaimer, the term of this patent is extended or adjusted under 35 U.S.C. 154(b) by 511 days.

(21) Appl. No.: 13/668,246

(22) Filed: Nov. 3, 2012

(65) Prior Publication Data

US 2013/0204831 A1 Aug. 8, 2013

Related U.S. Application Data

(60) Provisional application No. 61/555,871, filed on Nov. 4, 2011.

(51) Int. Cl.
*G06N 5/04* (2006.01)
*G06F 19/24* (2011.01)

(52) U.S. Cl.
CPC .............. *G06N 5/047* (2013.01); *G06N 5/04* (2013.01); *G06F 19/24* (2013.01)

(58) Field of Classification Search
None
See application file for complete search history.

(56) References Cited

U.S. PATENT DOCUMENTS

| 8,428,397 | B1 * | 4/2013 | Brandt | .......................... 382/305 |
| 2005/0273266 | A1 * | 12/2005 | Nickel | .............................. 702/14 |
| 2010/0177944 | A1 * | 7/2010 | Madabhushi et al. | ........ 382/131 |

OTHER PUBLICATIONS

"Estimating mutual information", Kraskov et al, Physical Review E 69, The American Physical Society, 2004, 16 pages.*
"Detecting Novel Associations in Large Data Sets", Reshef et al, Science vol. 334, 16 Dec. 2011, pp. 1518-1524.*
"An Informational Measure of Correlation", E. H. Linfoot, Information and Control, vol. 1, Issue 1, Sep. 1957, pp. 85-89.*
"Information Theory and Optical Images", E. H. Linfoot, Journal of the Optical Society of America (JOSA), vol. 45, Issue 10, Oct. 1955, pp. 808-819.*
"A study of different wavelets in orthogonal wavelet division multiplex for DVB-T", S. L. Linfoot, Consumer Electronics, IEEE Transactions on, vol. 54, Issue 3, Aug. 2008, pages.*
International Report on Patentability, PCT/US2012/063464, Mar. 30, 2015.

* cited by examiner

*Primary Examiner* — Kakali Chaki
*Assistant Examiner* — Mai T Tran
(74) *Attorney, Agent, or Firm* — David H. Judson

(57) ABSTRACT

A method to identify a relationship between at least pairs of variables in a dataset generates a novel measure of dependence, referred to as a Maximal Information Coefficient (MIC), that captures a wide range of interesting associations (not limited to specific function types such as linear, exponential or periodic, or to all functional relationships), and that gives similar scores to equally noisy relationships of different types. MIC is based on the idea that if a relationship exists between two variables, then a grid can be drawn on a scatterplot of the two variables that partitions the data to encapsulate that relationship.

21 Claims, 21 Drawing Sheets

| DATA | MIC | MAS | MEV | MCN | NLS |
|---|---|---|---|---|---|
| | 1.00 | 0.00 | 1.00 | 2.00 | 0.00 |
| | 1.00 | 0.74 | 1.00 | 3.00 | 0.85 |
| | 1.00 | 0.89 | 1.00 | 4.00 | 0.96 |
| | 1.00 | 0.69 | 1.00 | 2.56 | 1.00 |
| | 0.79 | 0.16 | 0.70 | 6.91 | 0.11 |
| | 0.71 | 0.03 | 0.32 | 6.87 | 0.71 |
| | 0.46 | 0.19 | 0.22 | 6.98 | 0.46 |

IDENTIFYING ASSOCIATIONS IN DATA AND PERFORMING DATA ANALYSIS USING A NORMALIZED HIGHEST MUTUAL INFORMATION SCORE

CROSS-REFERENCE TO RELATED APPLICATION

This application is based on and claims priority from Ser. No. 61/555,871, filed Nov. 4, 2011.

COPYRIGHT STATEMENT

This application includes subject matter that is protected by copyright.

BACKGROUND OF THE INVENTION

Technical Field

The disclosed subject matter relates generally to identifying associations in large data sets.

Background of the Related Art

Mutual Information

The information-theoretic concepts of entropy and mutual information are well-known. The Shannon entropy of a discrete random variable X is a measure of its information content and is defined by $$H(X) = -\sum_{i=1}^{B} p(x_i)\log p(x_i) \quad (0.1)$$

where $x_1, \ldots, x_B$ are the possible values of X.

Given two random variables, X and Y, their mutual information quantifies how much of the information in each variable can be explained by the other and is defined by:

$$I(X;Y) = H(X) + H(Y) - H(X,Y) \quad (0.2)$$

where H(X,Y) refers to the entropy of the ordered pair (X,Y), and can be re-written directly as:

$$I(X;Y) = -\sum_{i,j=1}^{B} p(i,j)\log\frac{p(i,j)}{p_x(i)p_y(j)} \quad (0.3)$$

where p is the joint probability distribution function and $p_x$ and $p_y$ are the marginal probability distribution functions of X and Y respectively. Intuitively, mutual information is a measure of the degree to which knowing the value of either variable gives information about the other. It has several properties that make it a desirable basis for a measure of association: it is invariant under order-preserving transformations of X and Y, it is always non-negative, and, most importantly, it equals zero precisely when X and Y are statistically independent.

The challenge in applying mutual information to detect relationships between two continuous variables lies in the fact that it is calculated over probability distributions. Methods for estimating the mutual information of the prior distribution of a set of measurements, called mutual information estimators, have been based on a range of techniques from histograms, to kernel density estimation, to clustering.

Mutual Information Estimation Using Gridding-Based Methods

Estimating mutual information from empirical data commonly involves two steps: estimating the joint distribution of the data, and then calculating the mutual information of that estimated distribution. Early methods for mutual information estimation impose a grid on the data in question to obtain an estimate of their joint probability distribution as illustrated in FIG. 1 (a). To this distribution they apply Equation 0.3 above to obtain a mutual information score. When formulating an approach to gridding the plot of a set of ordered points, there are two main questions to be considered: how many cells to allow in the grid, and where to place the grid lines. Equispatial partitioning (i.e. the histogram approach) simply chooses fixed numbers of rows and columns and splits the scatter plot into equal-sized rectangles. Equipartitioning (called adaptive partitioning in the literature) chooses fixed numbers or rows and columns and splits the scatter plot while attempting to place the same number of points in each row and column. Alternatively, the more advanced Fraser-Swinney algorithm continues refining its partition until a condition about the equi-distribution of the points in the cells is met. Similarly, algorithms for Bayesian bin density estimation can be used to evaluate the posterior probabilities of all possible binnings in estimating the joint distribution.

In addition to being heavily impacted by the partitioning method chosen, grid-based approaches are significantly affected by the numbers of rows and columns of the chosen grid (FIG. 1 (b-d)). To illustrate this point, imagine a set of 1000 uniformly distributed points in the x-y plane. If each axis is partitioned in half (making 4 total "boxes") then each quadrant of the x-y plane will have approximately the same number of points in it, and the estimated mutual information of this distribution is very close to zero. If, on the other hand, each axis is partitioned into 1,000 pieces (making a total of $10^6$ boxes), most of the columns will contain close to one non-empty box and the same is true for most of the rows. This will lead to a very high mutual information score since knowing the column in which a point falls is almost tantamount to knowing the row in which it falls and vice versa. This illustrates a standard dilemma in density estimation: if the number of partitions used is too small, then only very coarse details of the data become visible, but if it is large, then spurious fine details receive too much emphasis, resulting in artificially high mutual information scores.

When attempting to estimate the mutual information of a distribution given a finite set of points drawn from that distribution, equipartitioning performs significantly better than equispatial partitioning provided the numbers of rows and columns are large enough and the sample size is even larger. However, as discussed above both of these methods suffer from the fact that the numbers of rows and columns chosen affect the resultant scores. The Fraser-Swinney algorithm does not provide a significant improvement over either method. Finally, in cases where $N \ll M_{XY}$, approaches like Bayesian bin density estimation tend to work well.

Limitations of Mutual Information

Mutual information is a nonparametric statistic that is designed to detect any deviation from statistical independence, regardless of the form of that deviation. Because of this attractive property, mutual information has been used in several settings to measure the strength of associations of specific types. However, it has not been effectively used to compare relationships of different types to each other. This is because the mutual information of different types of functional relationships depends heavily on the specific functions governing those relationships. Simply put, not all functions preserve information to the same extent. For example, a perfect linear relationship has a higher mutual information than a perfect parabolic one because a linear function maps every x value to a unique y value while a parabolic function does not.

Mutual information does not give a meaningful measure of the strength of a dependence that can be compared across relationship types. The aim of all of the above mutual information estimation methods is to accurately estimate the mutual information of the "true" distribution governing a set of sample points. However, given that different distributions have inherently different mutual information scores, mutual information, no matter how well estimated for a given set of points, is not sufficient for comparing different distributions. This limitation has prevented the realization of the full potential of mutual information to detect a wide range of relationships.

Finally, not only is the mutual information of different classes of distributions different, but mutual information estimation is sensitive to sample size, making it very difficult even to compare the mutual information scores of the same types of distributions with different sample sizes. This, compounded by the fact that mutual information is unbounded and grows to infinity with increased sample size, makes interpreting mutual information scores extremely difficult in most settings. Mutual information can of course be normalized, but the differences between differential entropy and discrete entropy limit the scope of normalized mutual information variants that employ entropy to discrete random variables.

In this application, the partiality of a statistic will refer to a tendency of that statistic to give higher scores to certain relationship types (i.e. lack of equitability). A practical example of how the partiality of mutual information affects its ability to agnostically score different types of relationships can be observed using a dataset containing data from the World Health Organization about all the countries in the world (which is explored further below as a detailed example of the application of the disclosed subject matter). FIG. 7($i$) shows a quartet of relationships from the WHO dataset. Of these four relationships, the left two appear relatively noiseless while the right two appear more noisy. However, mutual information as estimated by Kraskov et al. assigns the top two relationships similar scores and assigns the bottom two relationships similar scores as well.

BRIEF SUMMARY

According to this disclosure, a method to identify a relationship between at least pairs of variables in a dataset generates a novel measure of dependence, referred to as a Maximal Information Coefficient (MIC), that captures a wide range of interesting associations (not limited to specific function types such as linear, exponential or periodic, or to all functional relationships), and that gives similar scores to equally noisy relationships of different types. MIC is based on the idea that if a relationship exists between two variables, then a grid can be drawn on a scatterplot of the two variables that partitions the data to encapsulate that relationship.

In one embodiment, a dataset is searched to identify a pair of variables that have a relationship with one another according to an iterative process, typically carried out in a computing entity. The process begins by (a) iteratively evaluating combinations of placements of a fixed number of vertical and horizontal partitions of a two-dimensional scatterplot of the data, wherein each combination of vertical (y) and horizontal (x) partitions represent a grid of cells upon which data in the scatterplot induce a probability distribution whose mutual information can be calculated. Then, (b) based on the mutual information scores, a grid is identified that results in a highest mutual information score. Steps (a)-(b) are then repeated for each x-by-y grid resolution up to a maximum grid resolution. For each grid resolution, a normalized highest mutual information score is then stored in a matrix. A maximum value in the matrix is the maximal information coefficient (MIC).

The MIC statistic is useful to facilitate data analysis in a wide variety of fields. As will be described, the techniques described herein provide for analytical tools and methods that can be used to make sense of complex data sets and, in particular to identify and characterize structure in data. The approach provides the ability to agnostically mine emerging datasets to identify and classify significant correlations without constraining exploration to a serial hunt for preconceived relationships.

The foregoing has outlined some of the more pertinent features of the disclosed subject matter. These features should be construed to be merely illustrative.

BRIEF DESCRIPTION OF THE DRAWINGS

For a more complete understanding of the disclosed subject matter and the advantages thereof, reference is now made to the following descriptions taken in conjunction with the accompanying drawings, in which.

DETAILED DESCRIPTION

Introduction

Figure 1A:
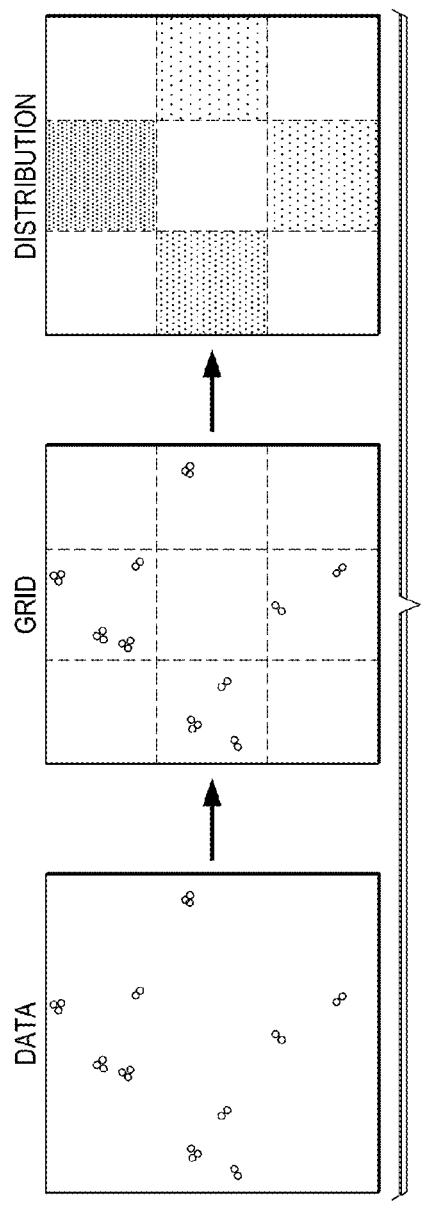
FIGS. 1$a$-1$d$ depict common types of relationships viewed using different grids.
Figure 1B:
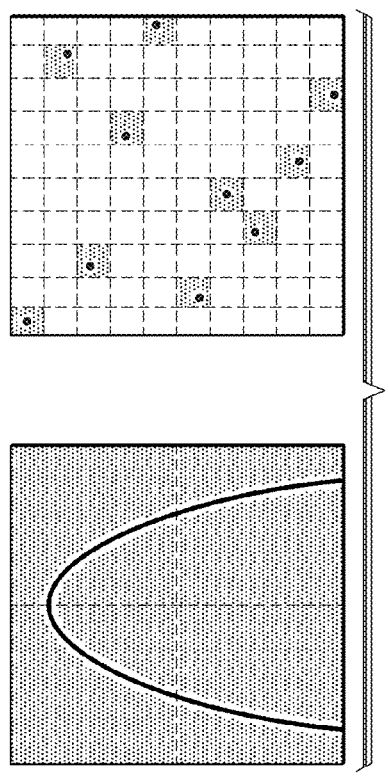

With an explosion of data in many fields, the challenge of identifying meaningful relationships between variables in large datasets is increasingly important. Furthermore, even the lesser goal of identifying pairwise relationships is a formidable one that is the subject of considerable exploration. This task is further complicated when different pairs of variables are related in different ways (e.g. linearly, exponentially, periodically, or even non-functionally).

One way to start exploring a large dataset is to search for the most closely associated pairs of variables in it. To do so we would ideally calculate some measure of relatedness for each pairwise relationship, rank the pairs by their scores, and then examine the relationships at the top of the list. For this approach to work effectively, the statistic we use should have two heuristic properties. First, we want to capture any interesting relationship, not just relationships of certain types, so the statistic should detect a wide range of association types (we will call this generality). Second, we want the interpretation of a score to be intuitive and independent of the type of the relationship being scored. For example, our list of relationships may be so large that we can only manually scan through a small fraction of it, so we cannot afford to have noisy linear relationships ranked near the top of the list, while strong sinusoidal relationships get lost in the middle. Thus, we want the statistic to give equally noisy relationships similar scores regardless of relationship type (we will call this equitability). The concept of equitability is difficult to formalize for associations in general, but it has a clear definition in the basic case of functional relationships: a statistic is equitable on functional relationships if, provided sufficient sample size, it gives any two functional relationships with similar $R^2$ values similar scores regardless of the functions governing the relationships.

None of the existing nonparametric methods for detecting deviation from statistical independence achieve both generality and equitability. For example, nonparametric curve estimation methods such as smoothing splines and regression estimators tend to be equitable across functional relationships, but are not general. More general methods, such as principal curve-based methods, maximal correlation, distance correlation, and mutual information estimators, can detect broader classes of relationships but are not equitable even in the basic case of functional relationships.

Ideally, one would like to have a unifying approach, call it a measure of dependence $\delta$, to detect as wide a range of associations as possible (functional and non-functional), and whose value would match the level of noise in an association relative to that association's generating model without needing prior knowledge of the nature of the generating model itself. In other words, one shouldn't have to know the type of pattern one is looking for, in order to determine which method to use, in order to find it.

This disclosure describes a measure of dependence, the Maximal Information Coefficient (MIC), that is both general and equitable. MIC captures a wide range of associations both functional and not, and when applied to functional relationships MIC provides a score that roughly equals the coefficient of determination ($R^2$) of the data relative to the regression function. As MIC proves difficult to calculate in practice, this application also presents a heuristic dynamic programming algorithm for estimating it.

As will be described, MIC gives rise to a larger family of statistics, called Maximal Information-based Nonparametric Exploration (MINE) statistics. This class of statistics can be used not only to identify interesting associations, but also to characterize them according to properties such as nonlinearity, monotonicity, complexity, and the degree to which a relationship can be modeled by a function.

The Intuition Behind MIC

In the same way that maximal correlation maximizes $\rho(X,Y)$ over the space of all Borel measurable functions of X and Y, MIC attempts to maximize a normalized variant of mutual information over a set of grids applied to the support of (X,Y). MIC is based on the idea that if a relationship exists between two variables plotted on a two-dimensional scatter plot, then there is a grid that optimally partitions the data to capture that relationship.

Figure 1C:
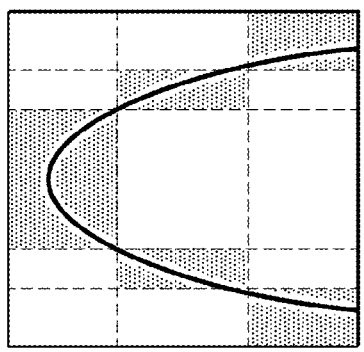
Figure 1C:
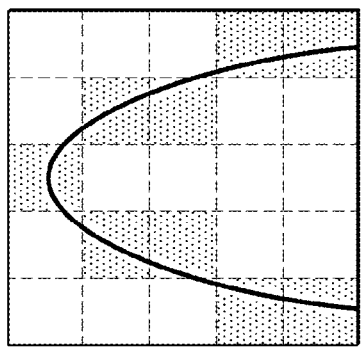
Figure 1C:
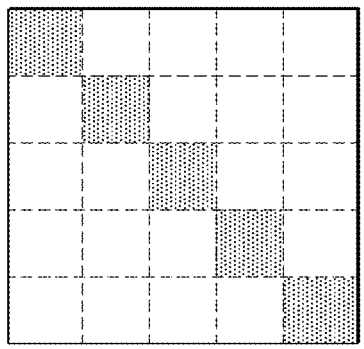
Figure 1D:
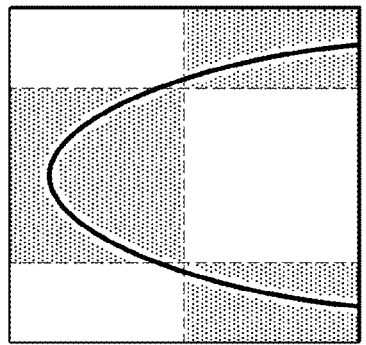
Figure 1D:
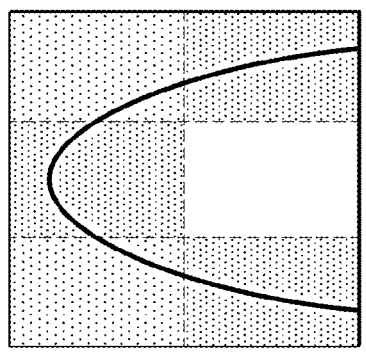
Figure 1D:
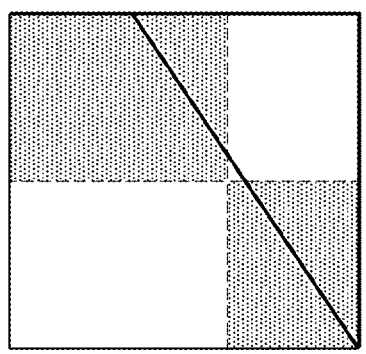
Figure 1D:
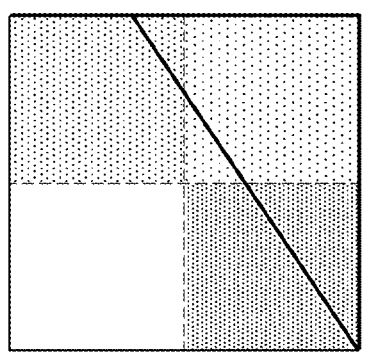

Returning to the above example, consider again a probability distribution derived by imposing a grid on a plot of a parabola and counting the relative numbers of points that fall into each cell. While it is not possible to have every row and column contain just one non-empty cell using a 5-by-5 grid, it is possible to draw a 3-by-5 grid such that at least the columns each contain only one non-empty cell (see FIG. 1(c)). With such a grid, we are still limited to a 50% success rate when guessing the column of a point based on its row (for all but the top row in this case), but we now can have a 100% success rate when guessing the row of a point based on its column.

MIC is predicated on the intuition that almost all functional relationships have a "right" grid that, when applied to their graphs, achieves a 100% success rate either in guessing the rows from the columns or vice versa. Correspondingly, the procedure for calculating MIC aims to examine grids with all possible numbers of rows and columns, drawn in all possible ways, in order to find the grid with the best success rate. The success rate is measured using a metric that is independent of the number of cells in the grid, thus allowing for comparison both between different grids and different functions. The result is the MIC, which detects a wide array of patterns—including all functional patterns—while filtering out variables that are statistically independent.

It is also instructive to consider the relation of MIC to normalized variants of mutual information. In order to apply a normalized variant of mutual information that uses entropy to continuous random variables, the probability density functions of the random variables should be discretized. But the appropriate resolution at which to discretize the data can depend on the joint distribution of the data as well as the sample size, and has significant effects on the estimation of both mutual information and entropy. MIC provides a method for applying a normalized variant of mutual information to continuous random variables by exploring a spectrum of discretization resolutions in search of the adaptive partition that is able to squeeze the most information out of the data.

Finally, examining the full spectrum of possible grids allows us to do more than simply find the right grid for every pattern. For example, because the parabola can achieve a 100% success rate with any grid containing n rows and 2n−1 columns, we can determine that most y-values are mapped to by two x-values. This sort of reasoning allows us to measure properties of a relationship such as monotonicity, nonlinearity, complexity, and the degree to which a relationship is functional. We will demonstrate that, by examining a relationship in this way using the full spectrum of possible grids, an approach called mutual information-based nonparametric exploration (MINE), we can not only find relationships, but also characterize them.

Defining MIC

Figure 2A:
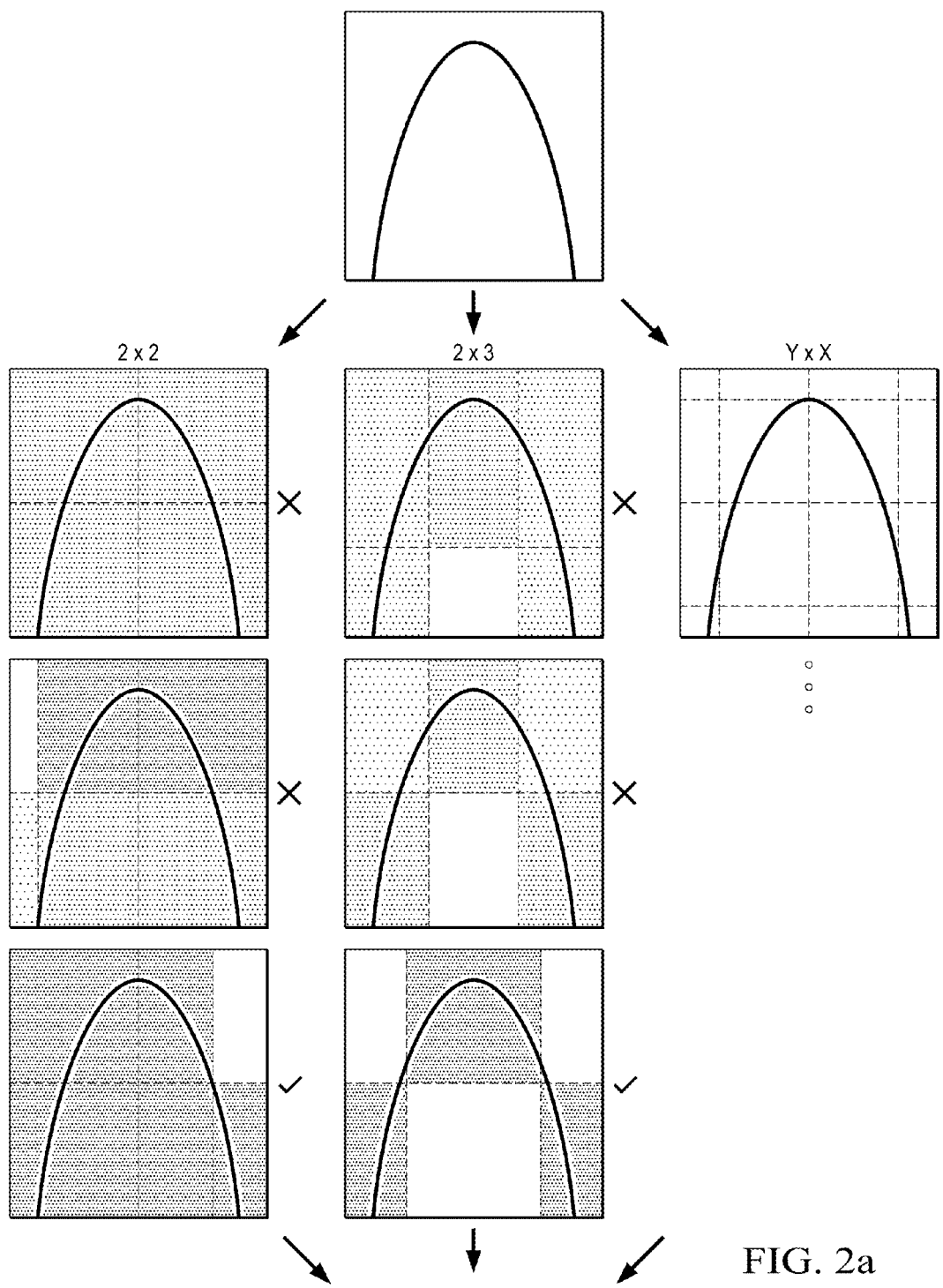
FIGS. 2$a$-2$c$ depict the process for the characteristic matrix and MIC, namely: (a) for each pair (x,y), the MIC algorithm finds the y-by-x grid with the highest induced mutual information, (b) the algorithm normalizes the mutual information scores, and compiles a matrix that stores, for each resolution, the best grid at that resolution and its normalized mutual information, (c) the normalized scores form a characteristic matrix, visualized as a surface; MIC corresponds to the highest point on this surface.
Figure 2B:
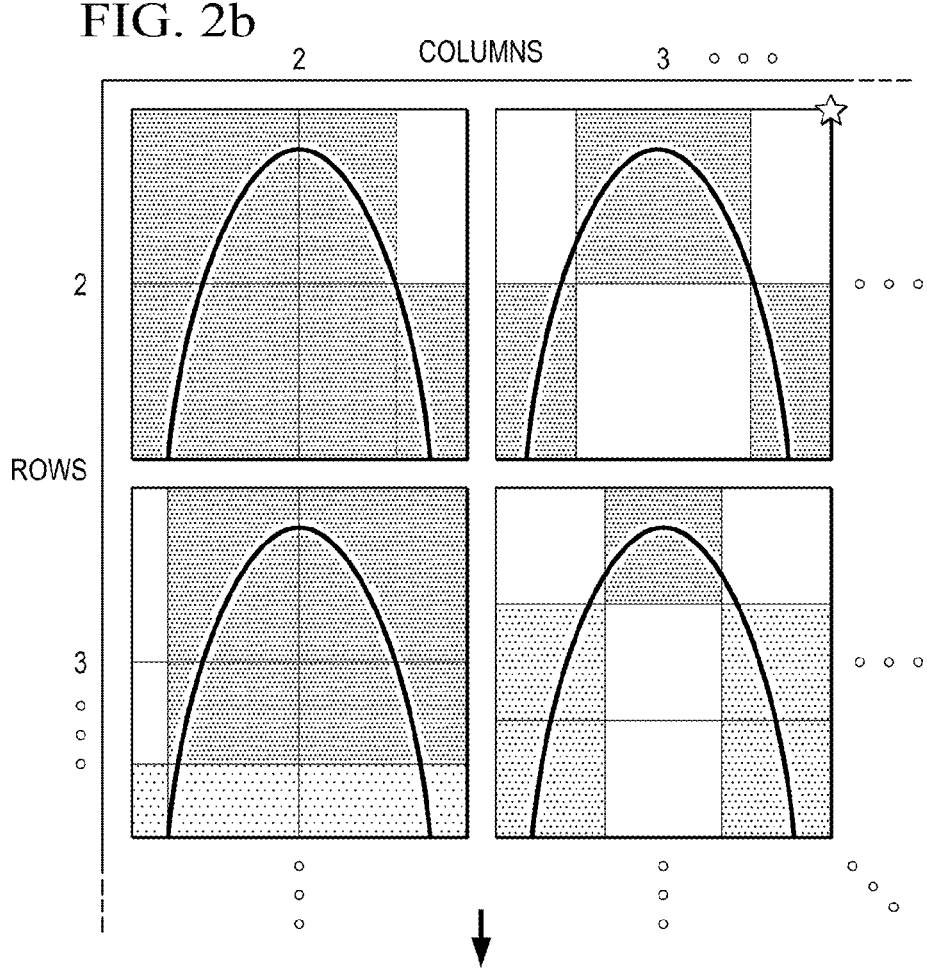
Figure 2C:
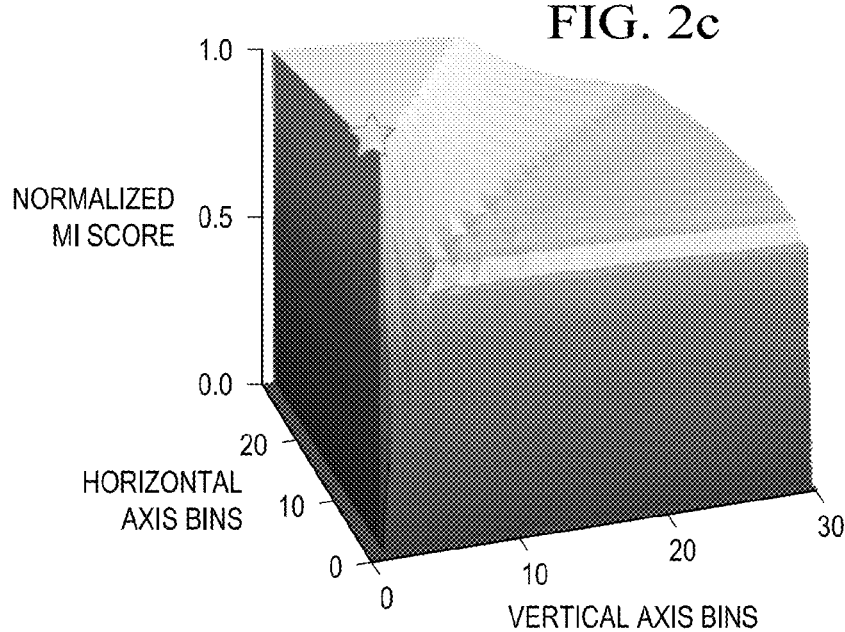
Figure 3A:
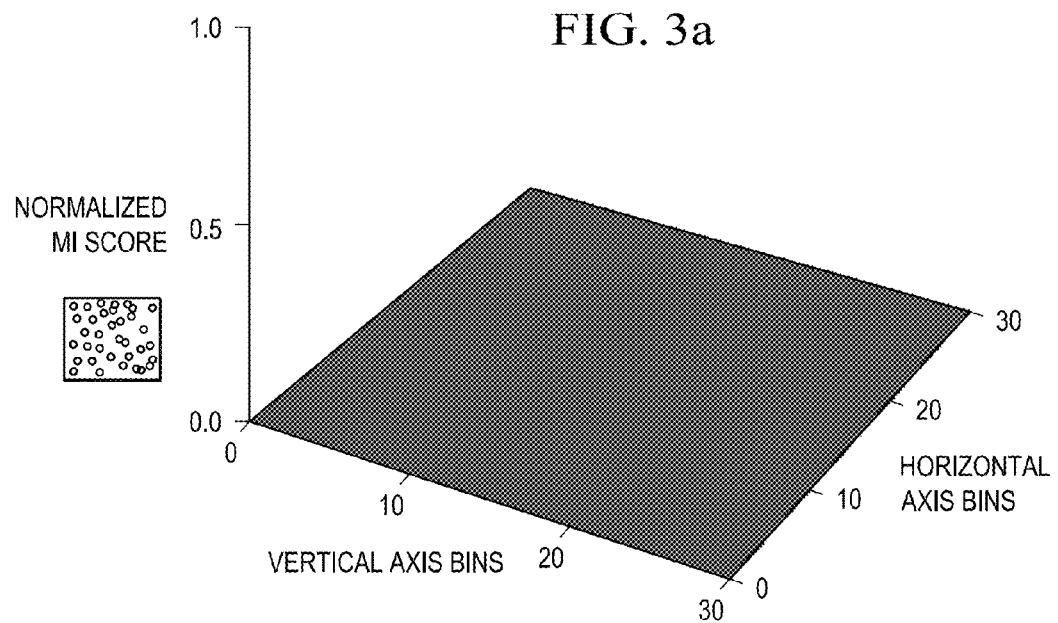
FIGS. 3$a$-3$f$ depict surfaces representing the characteristic matrices created when MIC is calculated for several common relationship types; for each surface, the x-axis represents number of columns (horizontal axis bins), the y-axis represents number of rows (vertical axis bins), and the z-axis represents the normalized score of the best-performing grid with those dimensions.
Figure 3B:
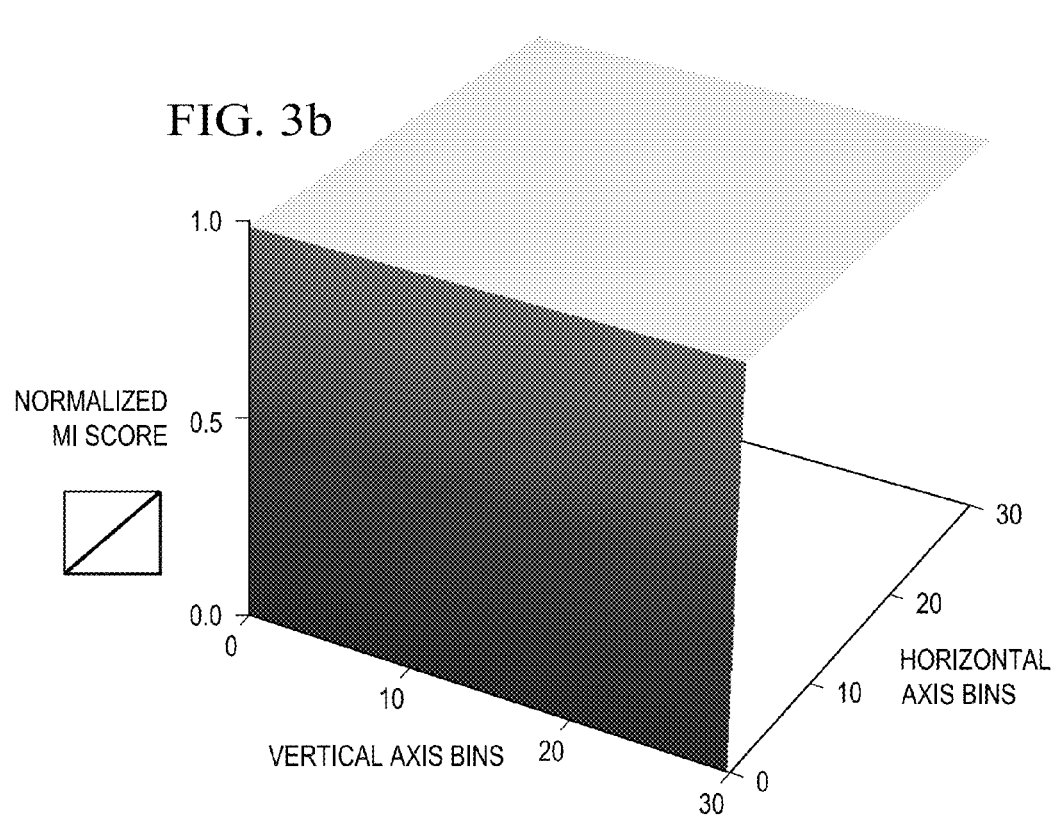
Figure 3C:
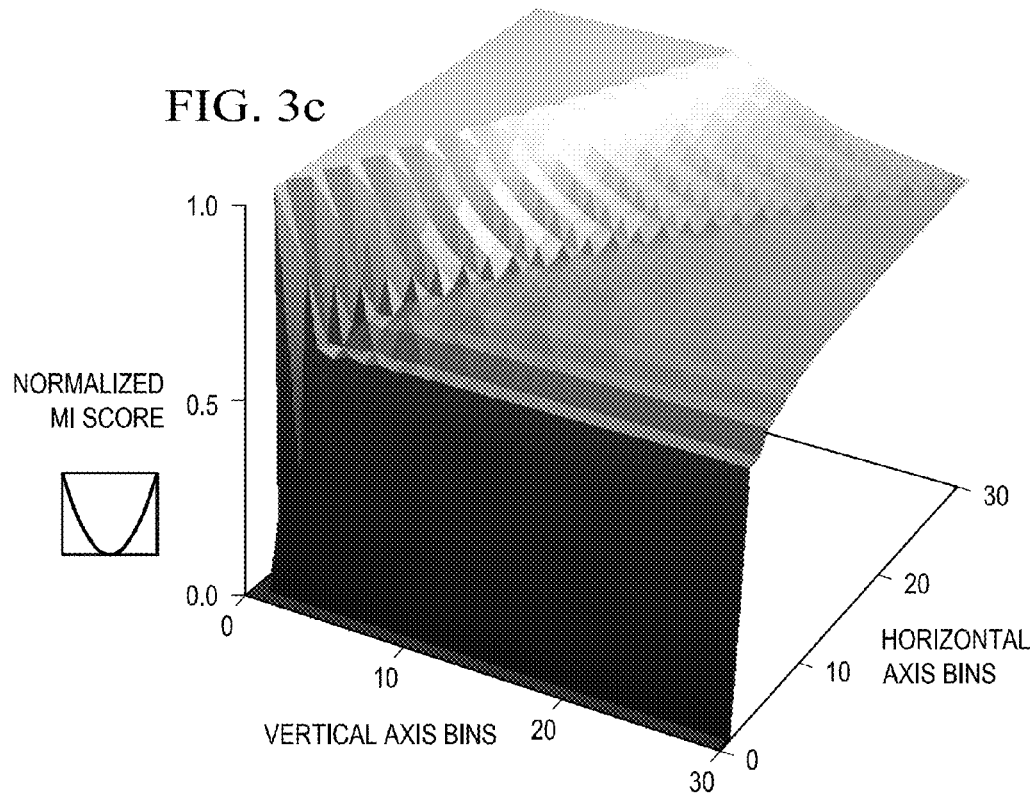
Figure 3D:
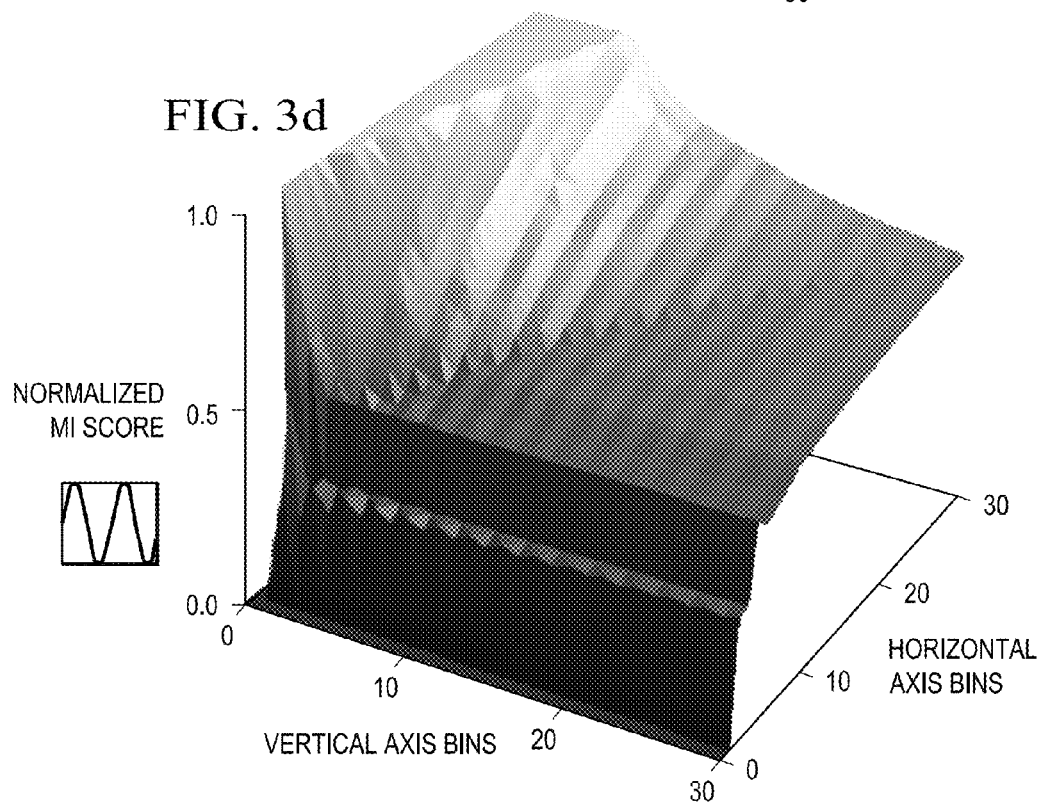
Figure 3E:
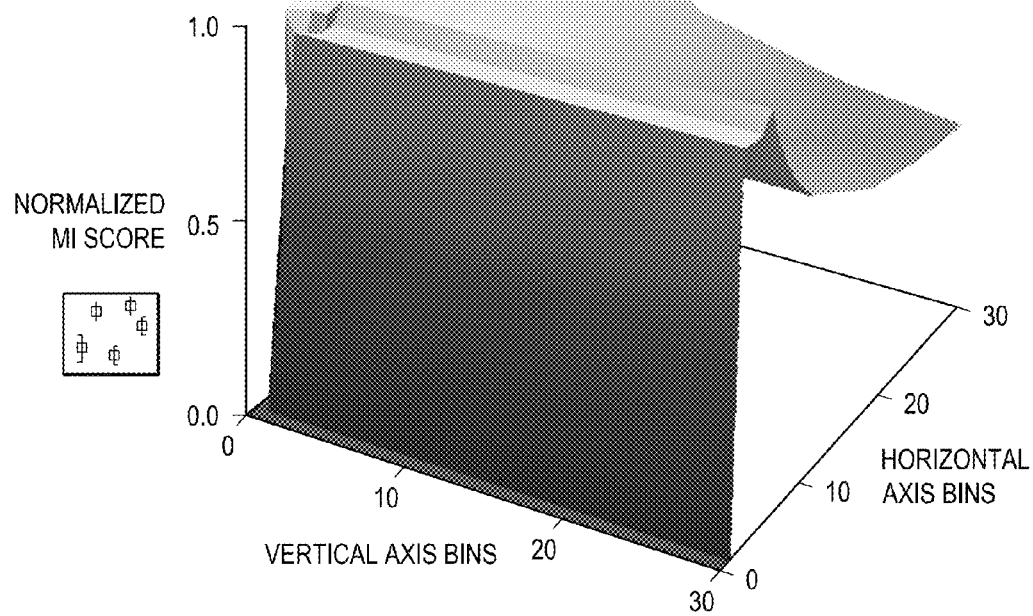
Figure 3F:
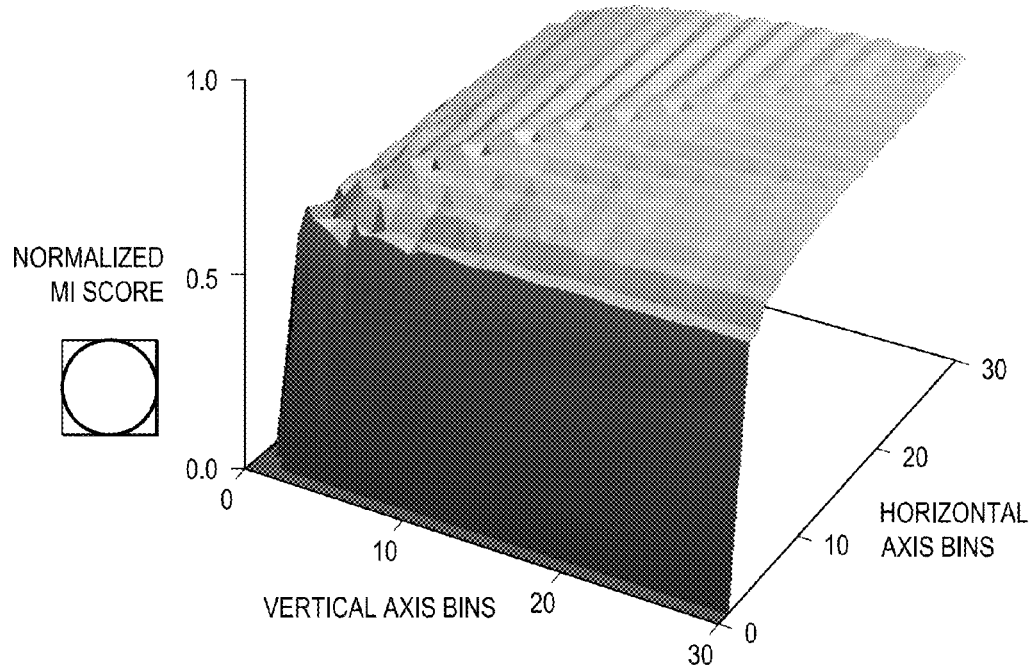

Informally speaking, MIC is based on the idea that if a relationship exists between two variables, then a grid can be drawn on the scatter plot of the two variables that optimally partitions the data to capture that relationship. Thus, to calculate the MIC of a set of two-variable data, D, we explore the space of all grids up to a sample-size dependent maximal grid resolution (FIG. 2 (a)), computing for every pair of integers (x,y) the largest possible mutual information achievable by any y-by-x grid. (Note that, while mutual information is used to quantify the performance of each grid, MIC is not an estimate of the mutual information of the joint distribution underlying the data.) We then normalize these maximal mutual information values in a way that ensures a fair comparison between grids with different dimensions, and results in a number between zero and one. The matrix whose (x,y)-th entry is the highest normalized mutual information achieved by any y-by-x grid is called the characteristic matrix, and MIC is the maximum value in it. (FIG. 2 (b,c)).

That is, the MIC of two-variable data D is calculated as follows. For each grid G with x columns and y rows such that $xy < B(n)$ (the parameter B(n) is discussed below):

(1) We convert G into the discrete random variable $D|_G$ described below.
(2) We measure the "amount of pattern" captured by G by computing the mutual information $I(D|_G)$. (The maximization of mutual information over all grids with x columns and y rows is discussed below.)
(3) We divide by log min{x,y}. (This normalization is discussed below.)

MIC(D) is then the highest normalized score achieved by any grid.

More formally, we can convert a set of measurements of a random variable X into a discrete random variable X' whose range is $[x]:=\{1, \ldots, x\}$ by partitioning the range of X into x bins and letting X'=i with probability equal to the proportion of measurements falling in the i-th bin. Given a set of two-variable data D, we can partition the range of x-values into x bins and the range of y-values into y bins. We call such a pair of partitions an y-by-x grid on the data, or a grid with x columns and y rows. Given such a grid G, we can calculate the mutual information of the resulting discrete random variable $D|_G$ using equation 0.3 above.

For any fixed set D of two-variable data, there are many different grids of the same dimensions which may have different corresponding values of mutual information. Thus, we can define I*(D,x,y) to be the maximum mutual information achieved by any grid with x columns and y rows on the data D. This allows us to define the characteristic matrix and the MIC of D.

Definition 0.1.

The characteristic matrix M(D) of a set D of two-variable data is an infinite matrix with entries $$M(D)_{x,y} = \frac{I*(D, x, y)}{\log \min\{x, y\}}.$$

Definition 0.2.

The Maximal Information Coefficient (MIC) of a set D of two-variable data with sample size n and total grid size less than B(n) is given by $$MIC(D) = \max_{xy<B(n)} \{M(D)_{x,y}\}.$$

Generally, B(n) is chosen so that $\omega(1) < B(n) \leq O(n^{1-\epsilon})$. In practice, setting $B(n) = n^{0.6}$ works well, and we discuss the role of B(n) further below.

An algorithm for calculating M(D) (and therefore MIC) is described below.

Methodological Issues

The Maximal Grid Size B(n)

Although we examine many grids to construct M(D), a point at which to stop should be chosen. The function B(n) upper bounds the sizes of the grids we search over. Determining the appropriate choice of B(n) is desirable, as setting B(n) too high can lead to non-zero scores even for random data because each data point gets its own cell, while setting B(n) too low means we are searching only for simple patterns (FIG. 1 (b)). These competing considerations can be balanced.

In one embodiment, the analyses set B(n) to be between $n^{0.55}$ and $n^{0.7}$, which works well in practice. In general, choosing a value for B(n) can depend on n.

Computing $I(D|_G)$

The mutual information estimation obtained from a scatterplot can vary widely depending on how the grid imposed on the plot is drawn, even if the numbers of rows and columns of that grid are fixed. For example, FIG. 1 (d) demonstrates how even a linear relationship can achieve a low score if a grid is drawn that does not correctly capture the pattern in the data. In an attempt to find the grid that would lead to the best approximation of the distribution from which the data were drawn, mutual information estimators have employed a variety of density estimation techniques. These methods include spatial partitioning of each axis, partitioning each axis so that each row/column contains approximately the same number of points, and employing clustering algorithms to find natural groupings of points on each axis. MIC takes a different approach to constructing grids: it searches for a partition that maximizes the estimated mutual information of D rather than attempting to approximate some "true" distribution of the data. In practice, this may be done using a heuristic dynamic programming algorithm to approximate the optimal grid for each fixed number of rows and columns.

Normalization

Just as mutual information is not directly comparable between functions, it is also not comparable between differently sized grids. This is because grids with more and more cells achieve higher and higher scores since their finer resolution makes them naturally more informative. There are several ways to normalize mutual information scores to address such issues.

The optimal grids found for different sets of data need not have the same dimensions. For example, a line can be captured perfectly by a two-by-two grid, but no two-by-two grid can perfectly capture a parabola. This is problematic because grids with different dimensions have different maximal mutual information scores: the maximal possible mutual information of a distribution on an y-by-x grid is log min{x,y}. Thus, even once an optimal grid is found for the line and for the parabola, they will yield different mutual information scores even though both are noiseless functions. Normalizing by log min{x,y} creates a score that can be compared across grids with different dimensions and therefore across different distributions. It also guarantees that almost all noiseless functions receive perfect scores and that the entries of the characteristic matrix range from zero to one. Examples of the characteristic matrices for several common functions are presented in FIG. 3.

The Characteristic Matrix and Other Statistics

Figures 4, 5:
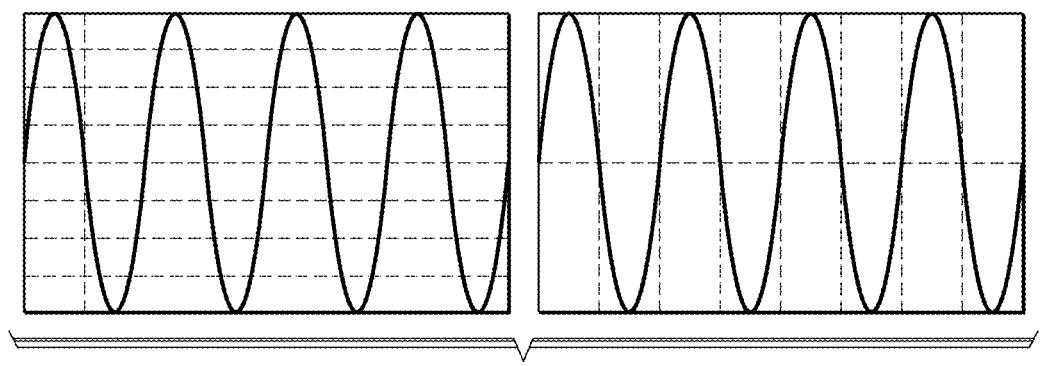
FIG. 4 contains MINE statistics for some functional and non-functional associations; MIC captures relationship strength; MAS captures departure from monotonicity; MEV captures closeness to being a function; MCN captures complexity; and NLS captures nonlinearity.
FIG. 5 contains a demonstration of the intuition behind MAS.
Figure 6A:
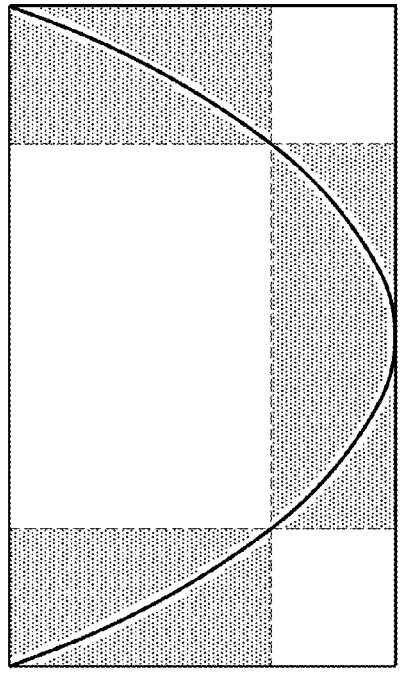
FIGS. 6$a$-6$d$ depict a demonstration of the intuition behind MEV.
Figure 6B:
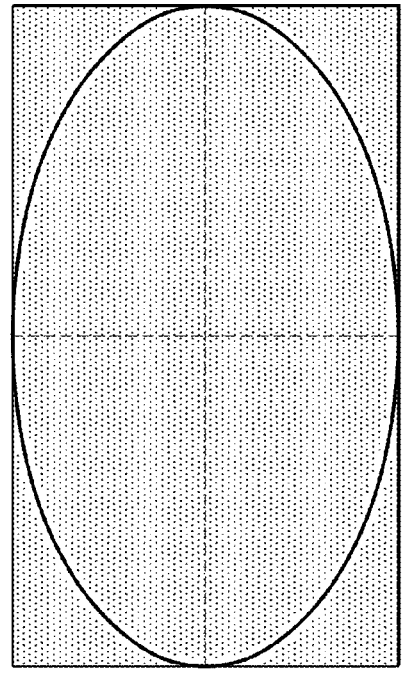
Figure 6C:
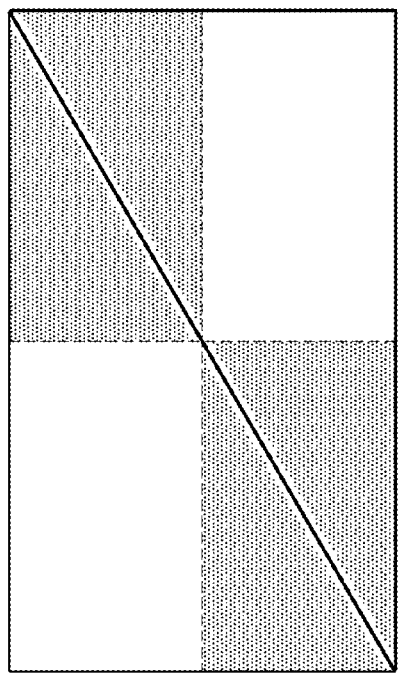
Figure 6D:
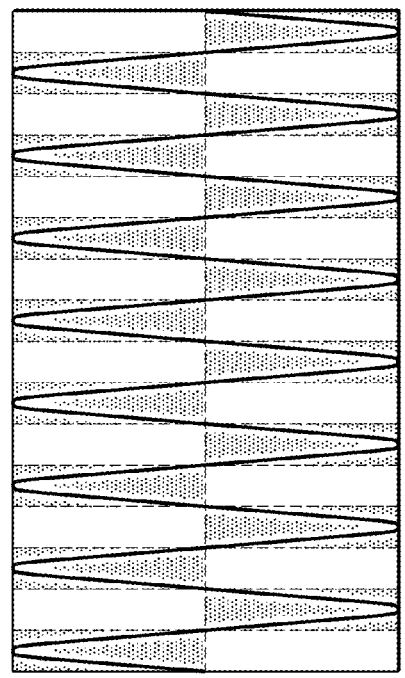
Figure 7A:
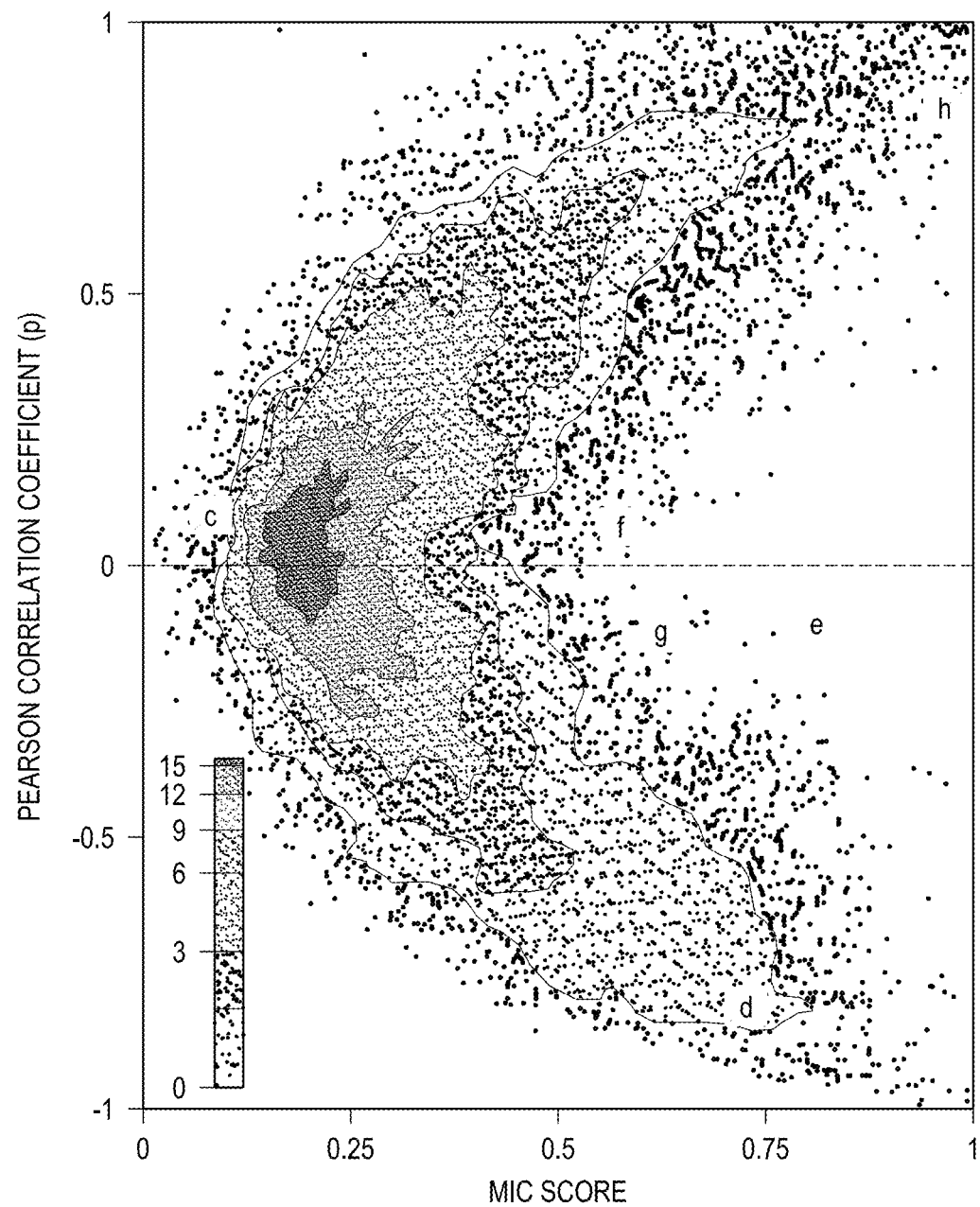
FIGS. 7$a$-7$i$ depict the application of MIC to the global indicators from the World Health Organization and partner organizations.
Figure 7B:
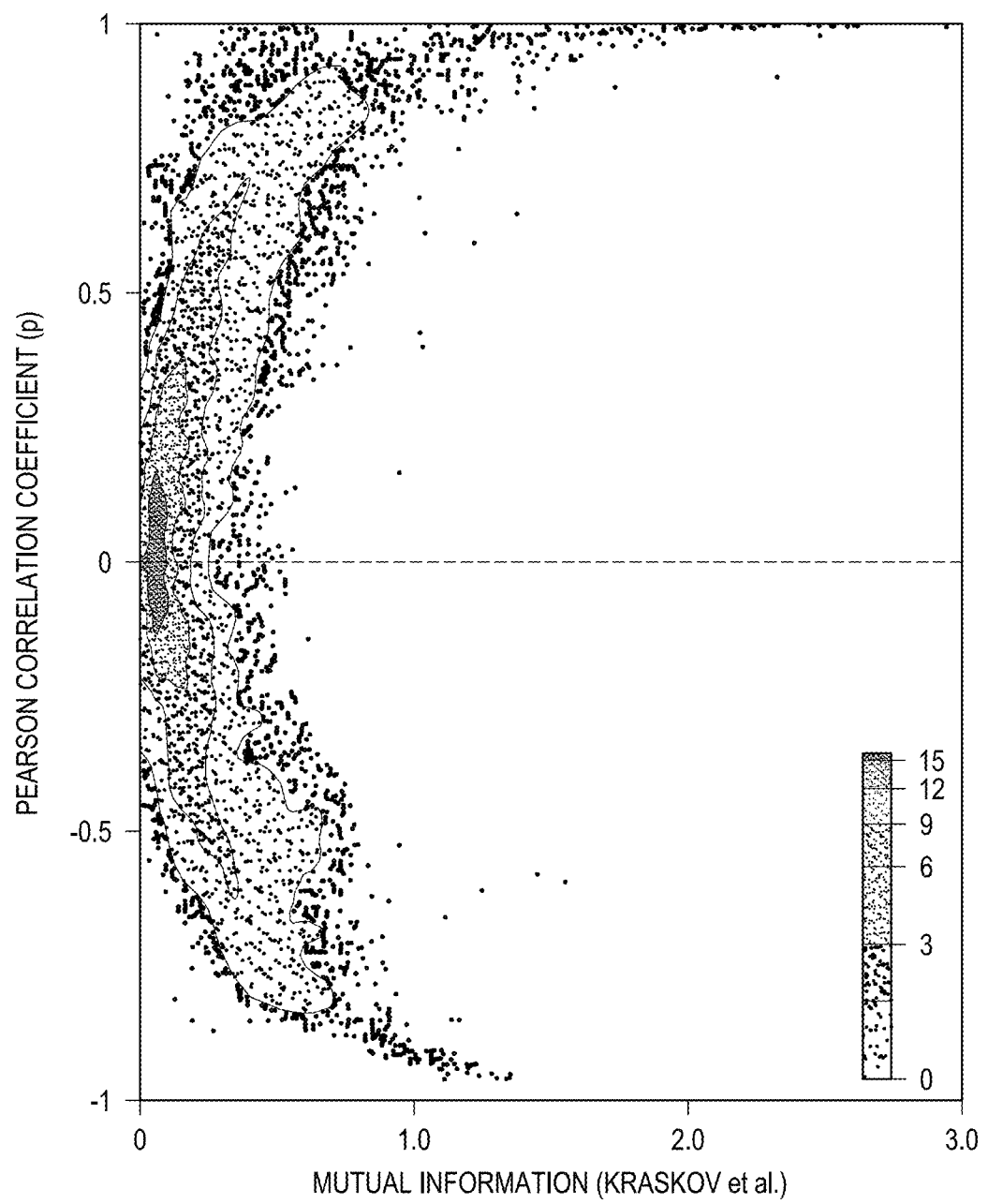
Figure 7C:
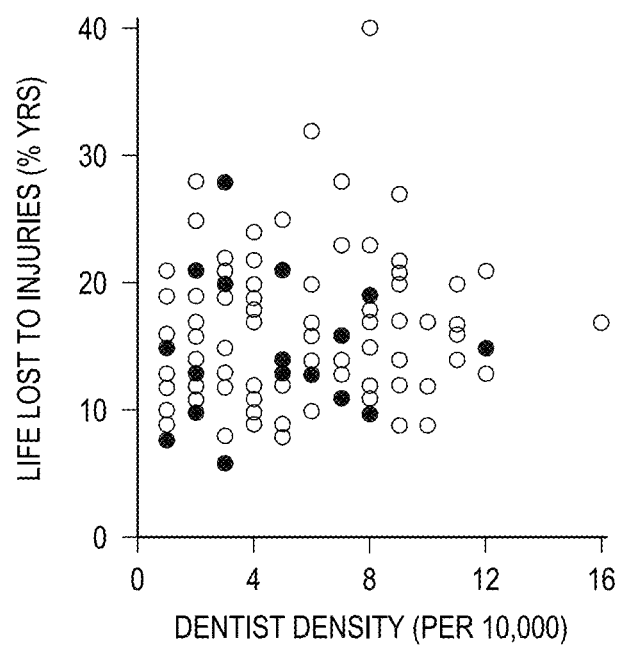
Figure 7D:
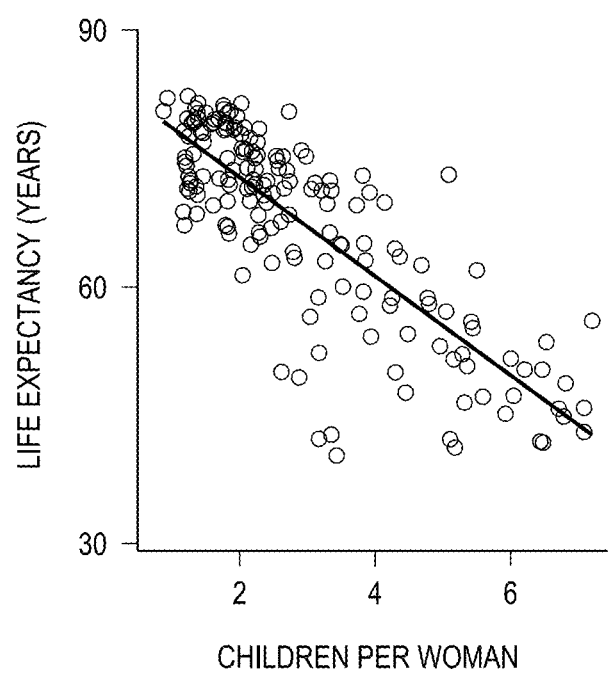
Figure 7E:
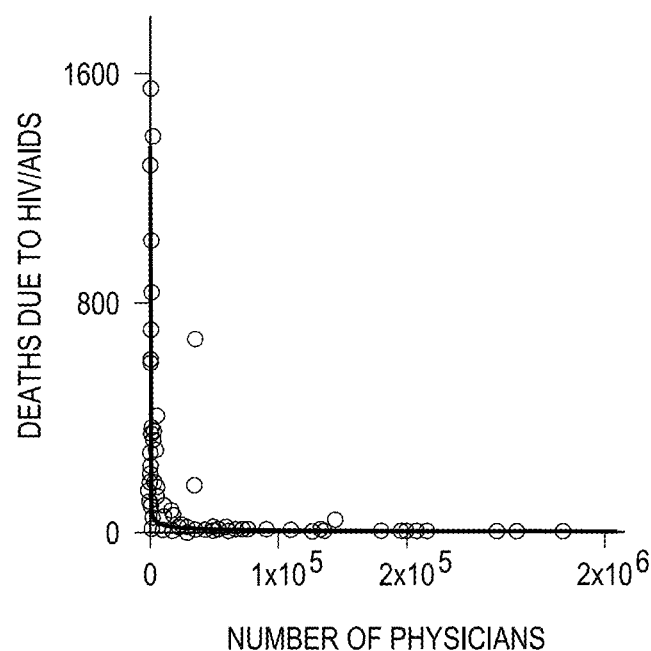
Figure 7F:
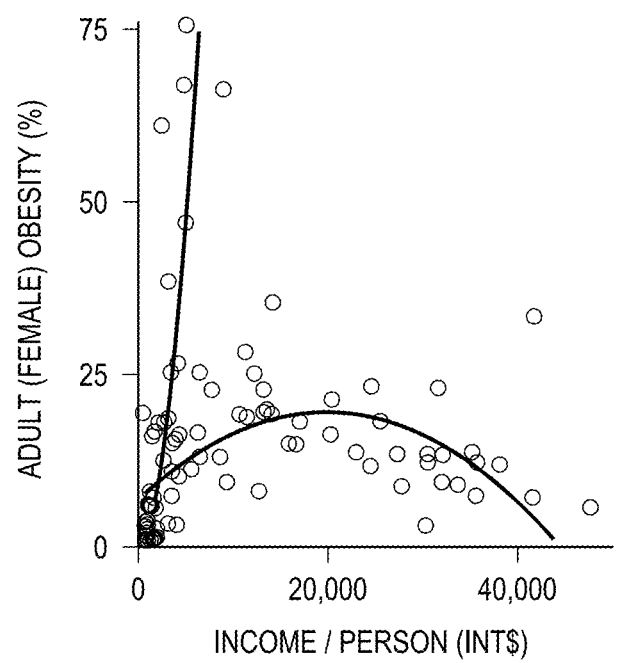
Figure 7G:
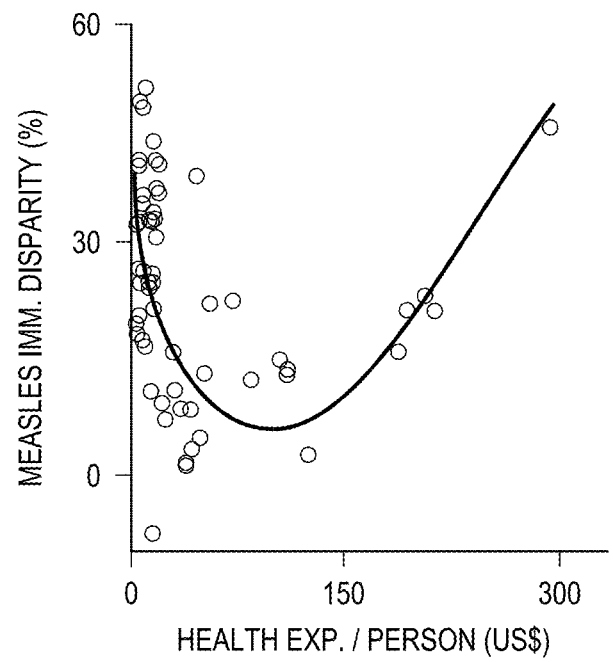
Figure 7H:
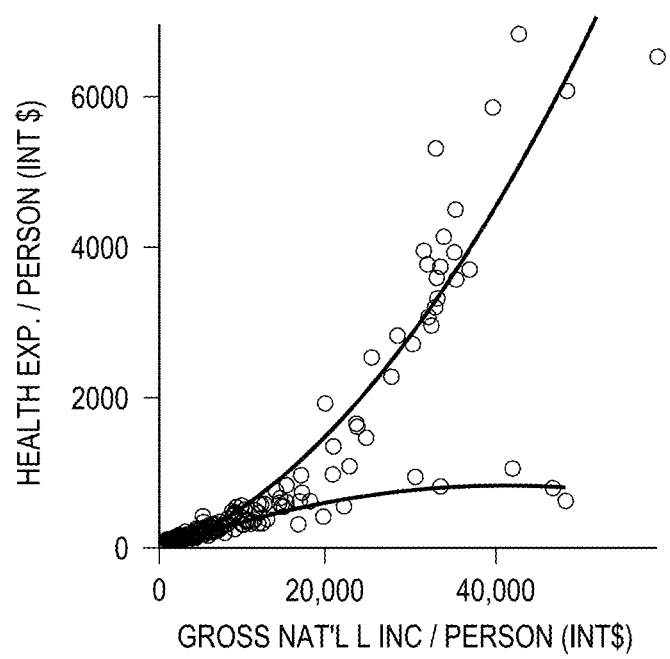
Figure 7I:
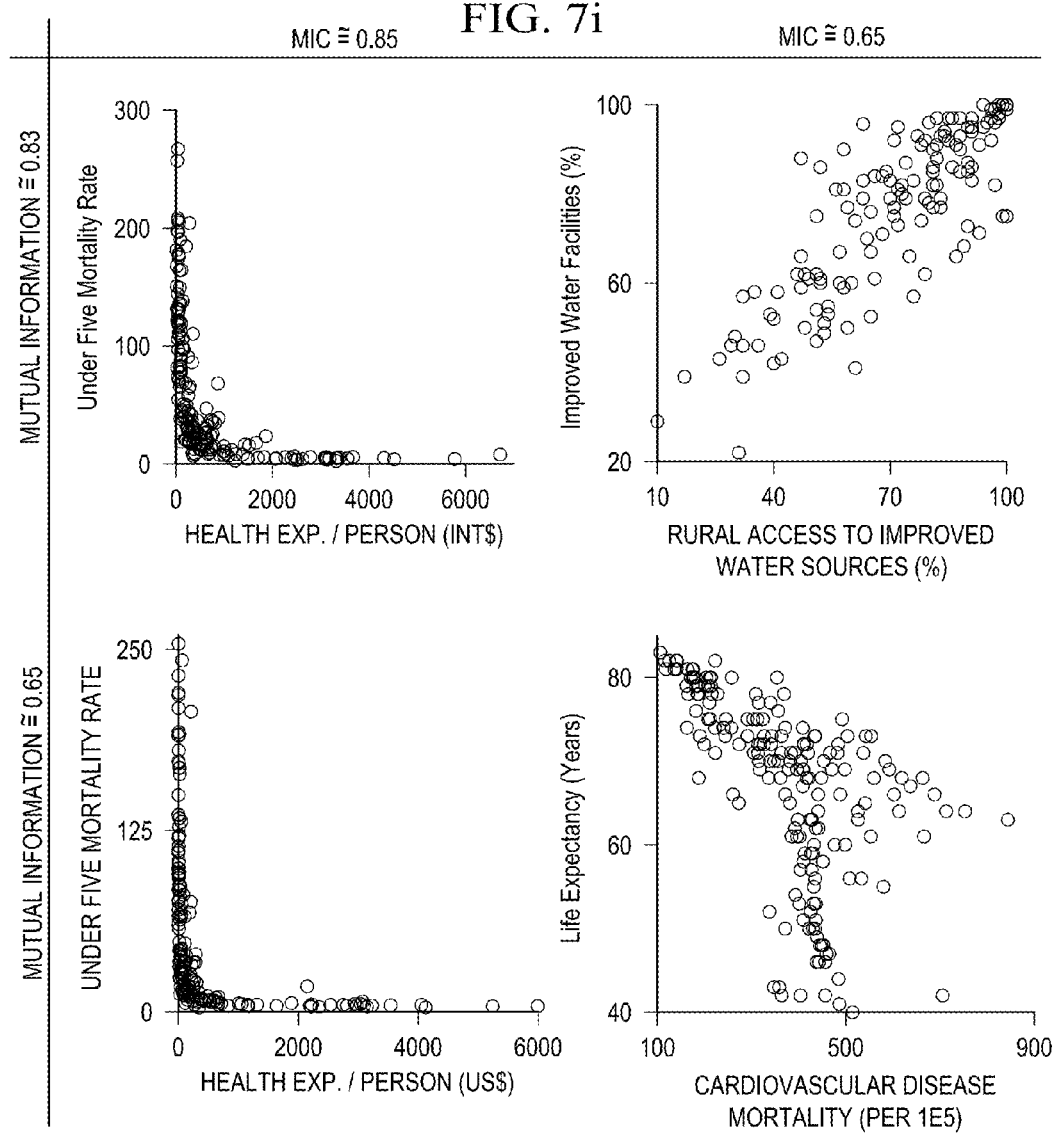
Figure 8A:
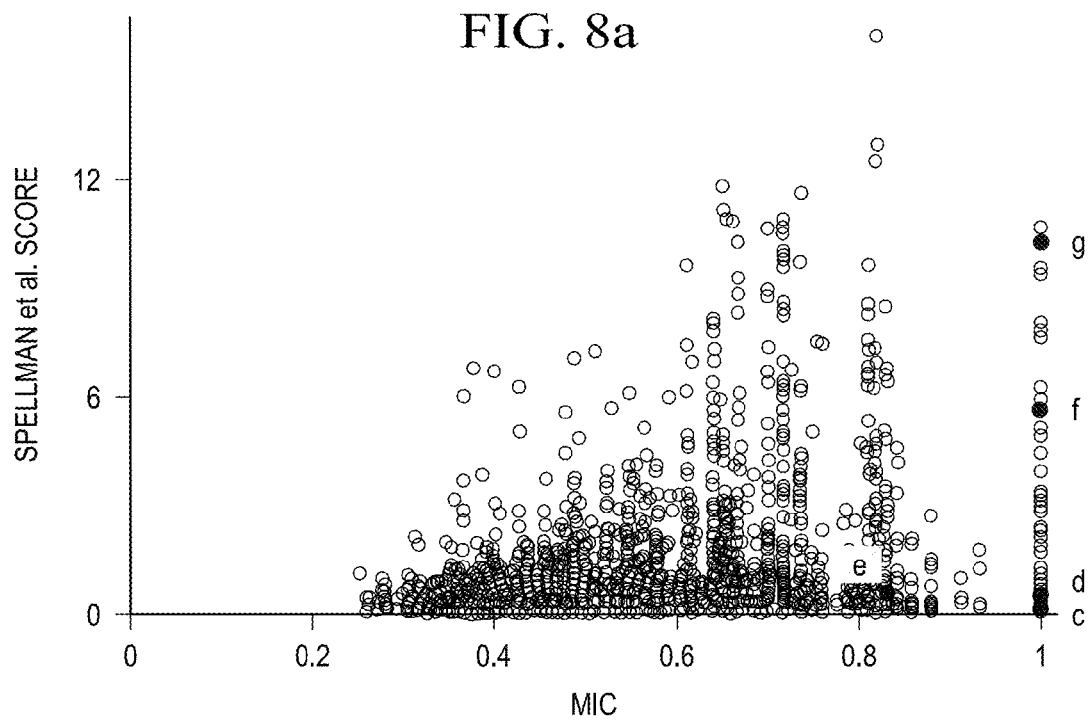
FIGS. 8$a$-8$g$ illustrate the application of MIC and MAS to S. cerivisiae gene expression data.
Figure 8B:
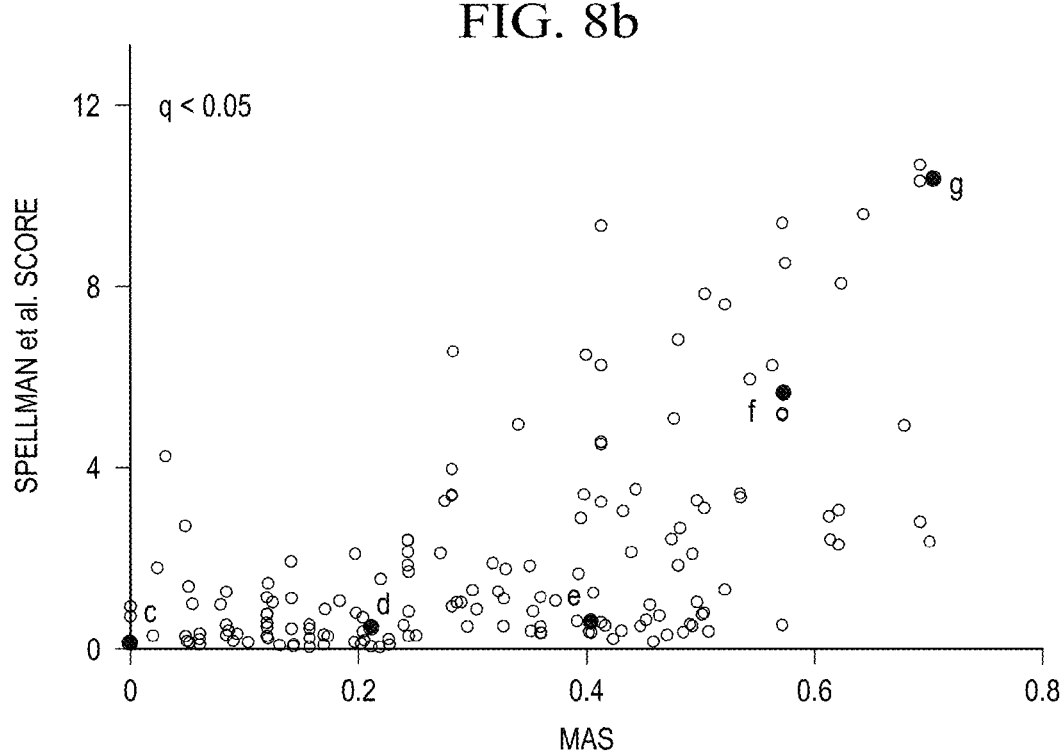
Figure 8C:
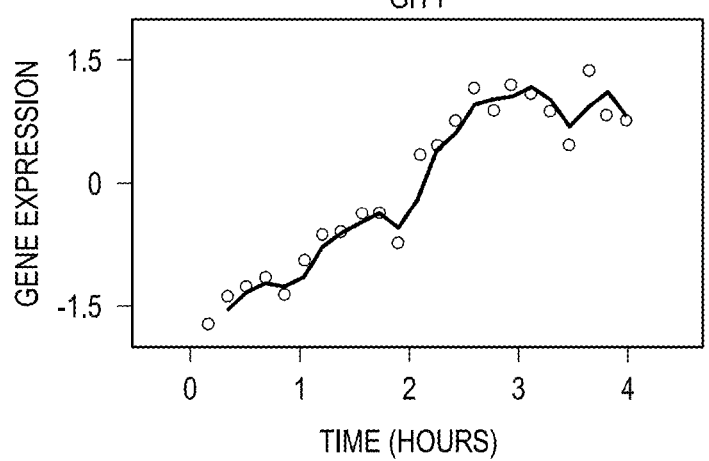
Figure 8D:
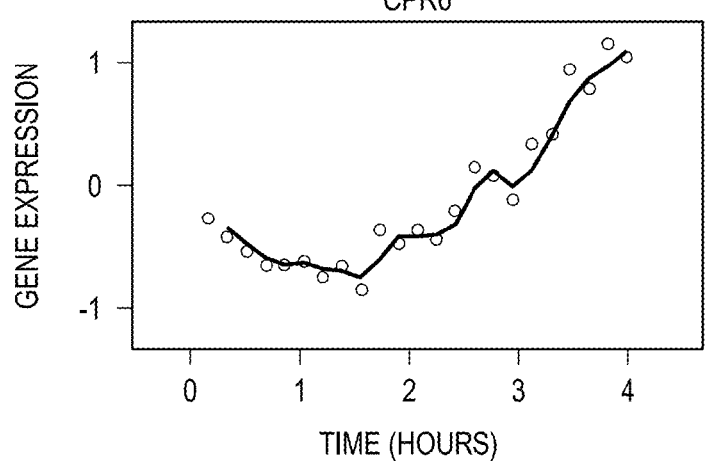
Figure 8E:
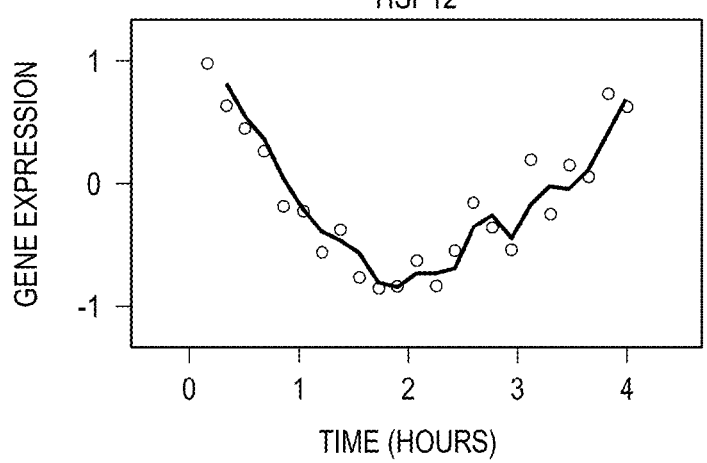
Figure 8F:
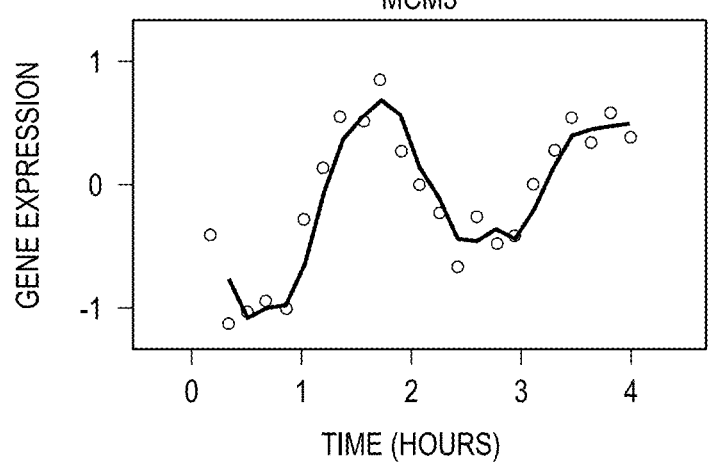
Figure 8G:
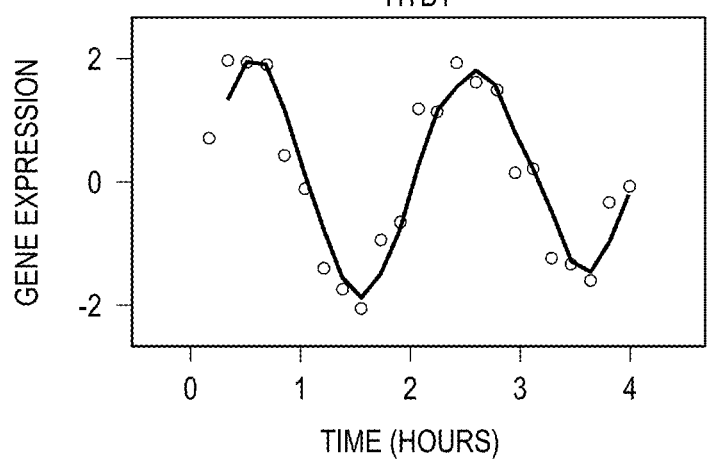
Figure 9A:
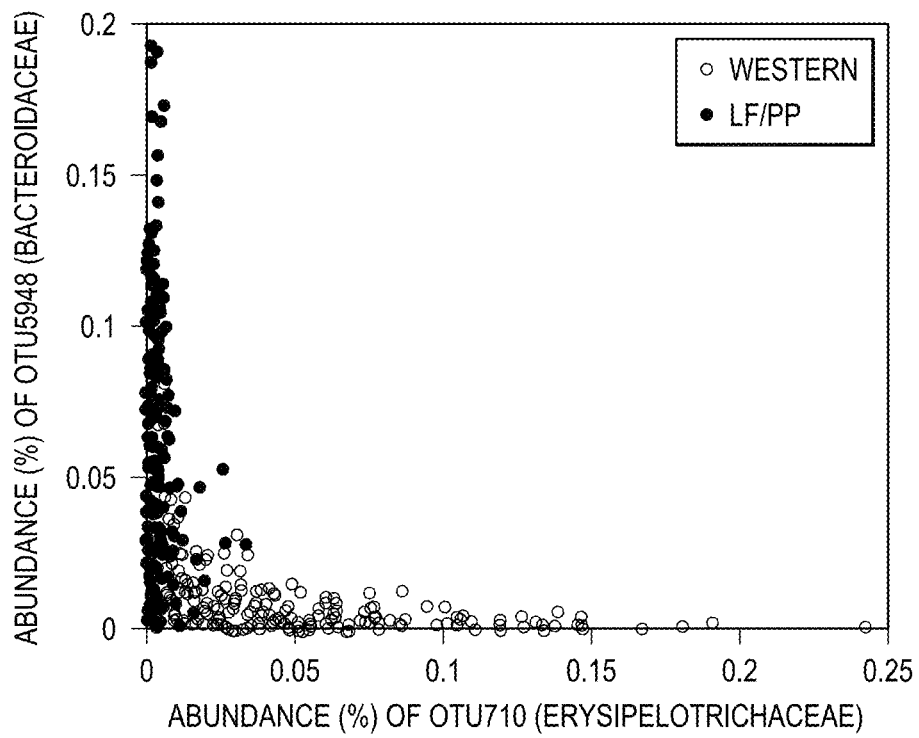
FIGS. 9$a$-9$e$ illustrate the results of applying MIC to detect associations between bacterial species in the gut microbiota of 'humanized' mice.
Figure 9B:
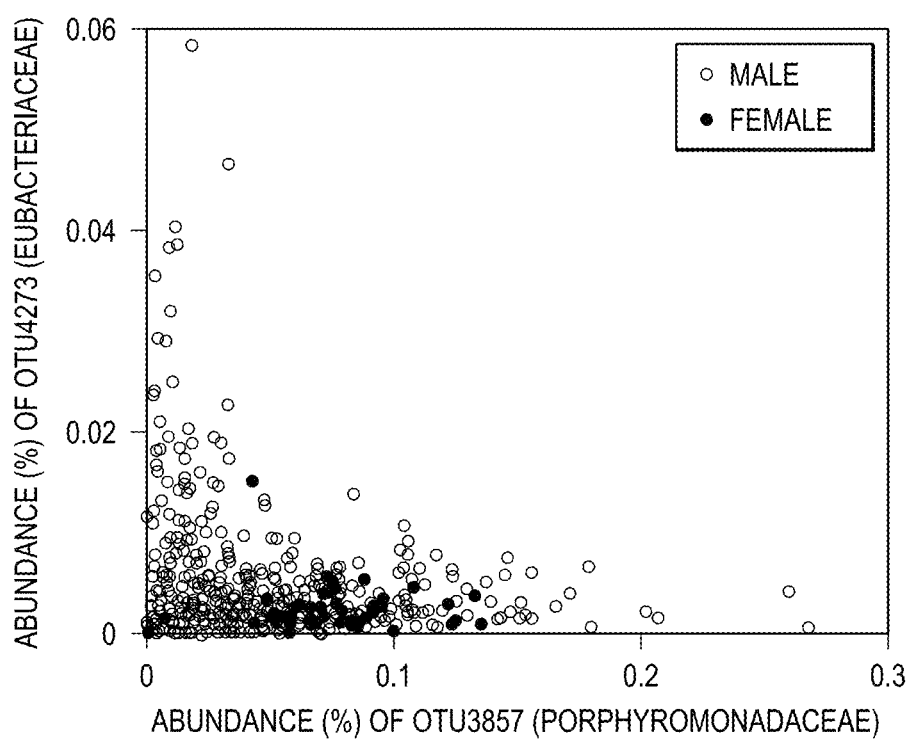
Figure 9C:
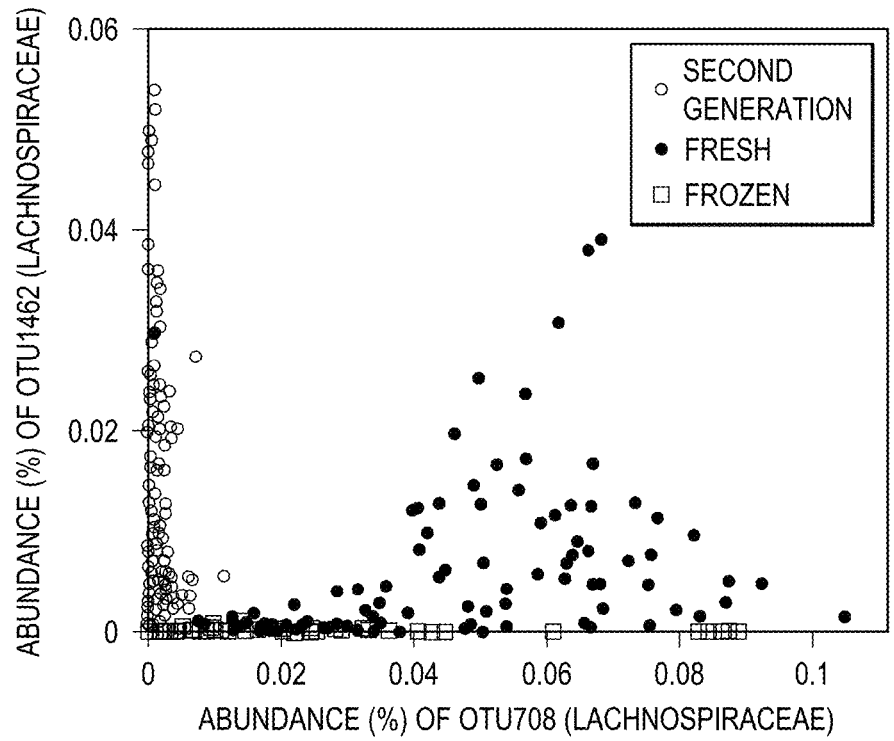
Figure 9D:
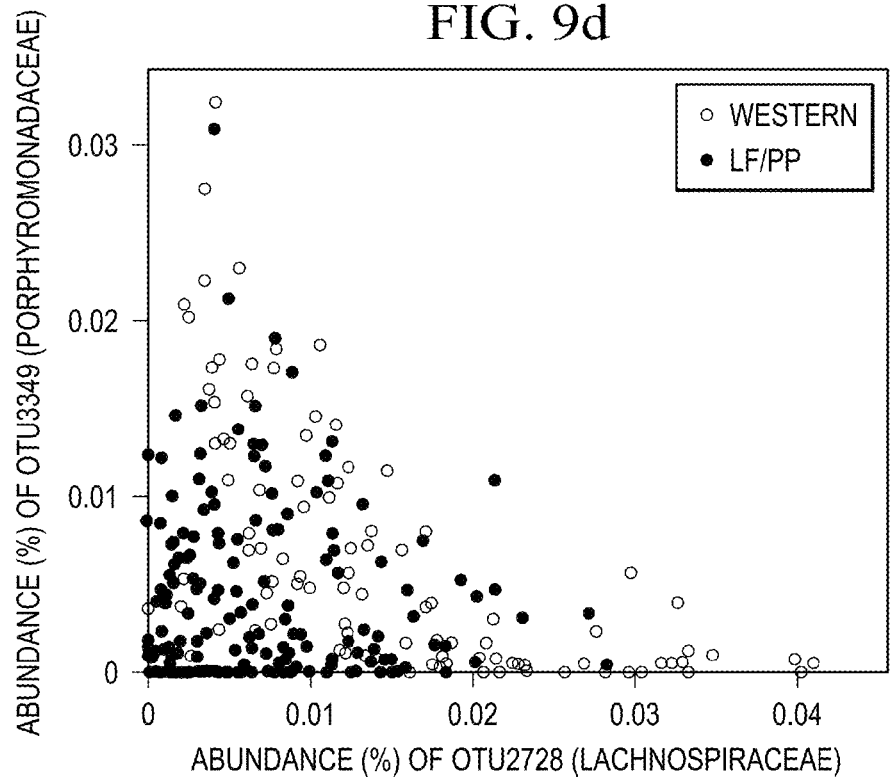
Figure 9E:
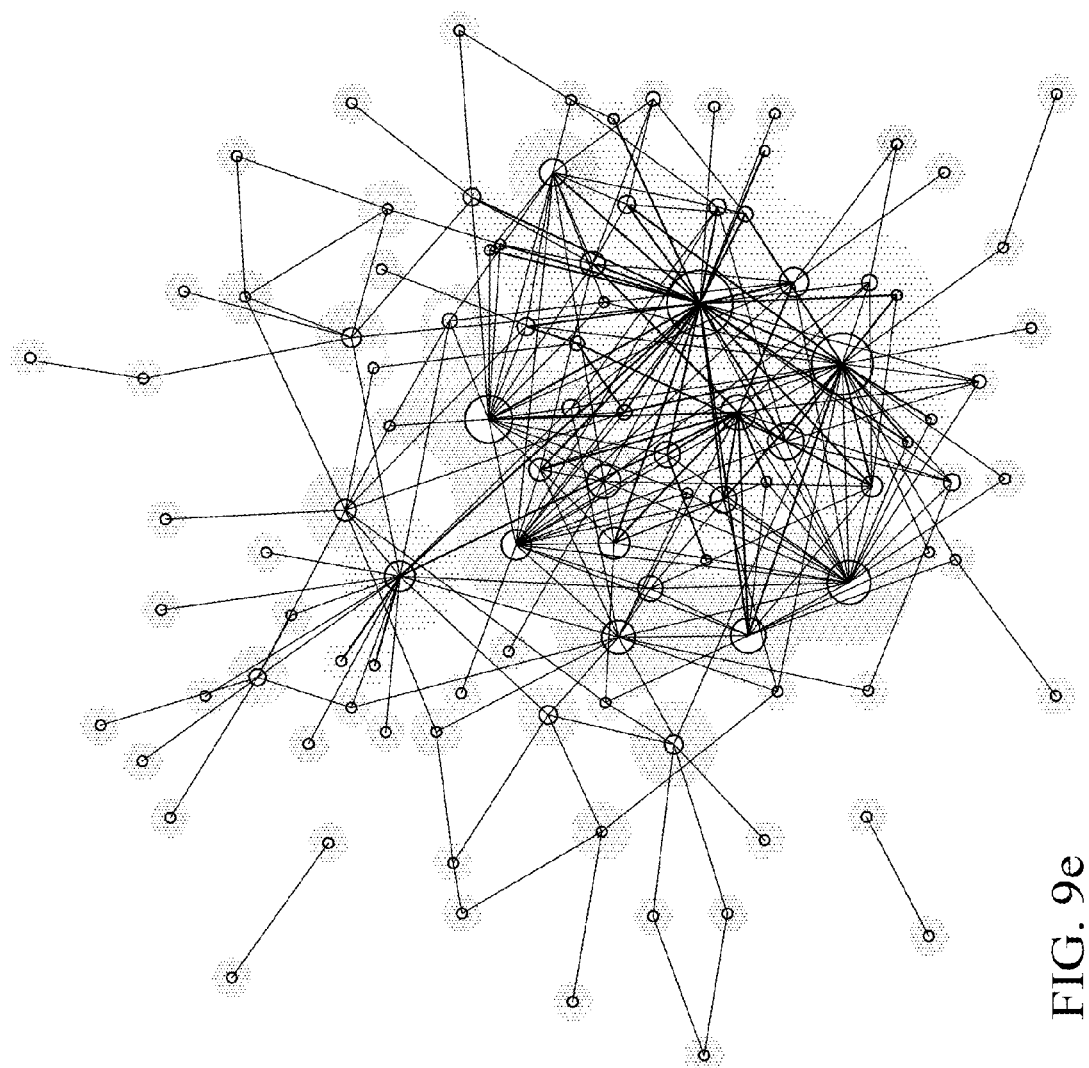

The properties of MIC and the characteristic matrix M used to calculate MIC enable the development of other statistics to further classify identified relationships. Recall that the characteristic matrix M of a set of data D is defined by $$M(D)_{x,y} = \frac{I*(D, x, y)}{\log \min\{x, y\}},$$

where $I*(D,x,y)$ is the maximum mutual information achieved by any grid with x columns and y rows on the data D. MIC is the maximum value of this matrix, but the matrix inherently contains much more information about D. We present a several additional statistics which can be derived from the characteristic matrix; further exploration of such properties of the characteristic matrix is a promising area for future research. FIG. 4 shows a few different patterns and their corresponding scores using these statistics.

Non-Monotonicity

A statistic that measures the symmetry of a characteristic matrix provides a measure of deviation from monotonicity. Intuitively, this is because a monotonic function can be expressed as a function of either axis: the value of a point along one axis uniquely specifies its value along the other. Monotonic functions therefore have completely symmetric characteristic matrices. Non-monotonic functions (e.g. parabola, sinusoid), on the other hand, have an asymmetry between the scores achieved when rows outnumber columns and vice versa (FIG. 5). We quantify this effect by measuring the Maximum Asymmetry Score (MAS), defined by $$MAS(D) = \max_{xy<B}|M(D)_{x,y} - M(D)_{y,x}|. \qquad (0.4)$$

MAS is never greater than MIC. For an illustration of the intuition behind MAS, see FIG. 5.

Closeness to being a Function

The Maximum Edge Value (MEV) is defined by $$MEV(D) = \max_{xy<B}\{M(D)_{x,y}: x = 2 \text{ or } y = 2\} \qquad (0.5)$$

and measures the degree to which the dataset appears to be sampled from a continuous function. Like MIC and MAS, it ranges from 0 to 1 with a score of 1 suggesting a well-behaved function. As in the case of MAS, we have MEV≤MIC always.

The intuition behind MEV is that if a set of data points "passes the vertical line test", in that for the imagined underlying distribution each vertical line can contain only one point, it should have a close-to-optimal grid with only two rows. Similarly we could consider a horizontal line test. On the other hand, when the underlying distribution for the data points does not pass either the vertical or horizontal line test, we have observed that the sampled datasets receive low scores when the grids are restricted to having only two rows or only two columns, as one would expect. For an illustration of the intuition behind MEV, see FIG. 6.

Complexity

The Minimum Cell Number (MCN) is defined by $$MCN(D, \epsilon) = \min_{xy<B}\{\log(xy): M(D)_{x,y} \geq (1 - \epsilon)MIC(D)\} \qquad (0.6)$$

This statistic measures the complexity of the relationship, in terms of the number of cells required to reach the MIC score. For example, a simple function like $f(x)=x$ requires very few cells (four, in fact) to grid in an effective way while a complex function such as $f(x)=\sin(18\pi x)$ requires many (thirty-six) cells. The $\epsilon$ parameter provides robustness and should depend on the MIC of the relationship in question. In FIG. 4, $\epsilon=0$ is set to 0 because the functions considered are noiseless. For the more general case, something like $\epsilon=1-MIC(D)$ may be a more appropriate parameterization.

Nonlinearity Score

We can take advantage of certain properties of MIC, such as equitability on functional relationships and monotonicity to define a natural measure of nonlinearity. The Nonlinearity Score (NLS) can be defined by:

$$NLS(D)=MIC(D)-\rho^2, \qquad (0.7)$$

where $\rho$ denotes the Pearson product-moment correlation coefficient. Because MIC takes values between zero and one and roughly equals $R^2$ relative to the regression function for functional associations, this quantity $MIC-\rho^2$ serves as a good measure of the degree to which the strength of an association is due to a linear correlation.

Variants of the Characteristic Matrix and MIC

The characteristic matrix (and therefore MIC) is defined using a normalization by log min{x,y}, as this represents the upper bound on the mutual information of a distribution on an y-by-x grid. However, for discrete random variables, $I(X,Y)\leq\min\{H(X),H(Y)\}\leq\log\min\{x,y\}$. This could in principle lead to variants of the characteristic matrix which use different normalizations, such as min{H(X),H(Y)} or any other normalization of discrete mutual information. The characteristic matrices of these variants may differ from the characteristic matrix defined above, and their properties may by used to gain additional or different information about the data from which they were calculated.

In the case of the characteristic matrix defined above, normalizing by log min{x,y} as opposed to min{H(X),H(Y)} results in normalizing the maximized mutual information at each grid resolution by the marginal entropy of a uniform distribution rather than by the minimum of the true marginal entropies. The choice of normalizing by log min{x,y} rather than min{H(X),H(Y)} provides useful advantages.

The Algorithm for Generating the Characteristic Matrix

The Idealized Algorithm

We have now explored several properties of the characteristic matrix, but we have not yet discussed how to generate it. As shown below, we can use dynamic programming to heuristically generate M(D), and in turn MIC and the rest of the MINE statistics, which works efficiently in practice.

We begin by outlining an idealized algorithm for generating the characteristic matrix. Algorithm 1 represents the ideal algorithm.

---
Algorithm 1 CharacteristicMatrix(D, B)
---
Require: D is a set of ordered pairs
Require: B is an integer greater than 3
 1: for (x, y) such that xy ≤ B do
 2:   $I_{x,y}$ ← MaxMI(D, x, y)
 3:   $M_{x,y}$ ← $I_{x,y}$/min{log x, log y}
 4: end for
 5: return {$M_{x,y}$ : xy ≤ B}
---

Line 3 is the normalization step. Using the scores returned by Algorithm 1, MIC, MAS, and the other statistics are straightforward to calculate from their mathematical definitions.

The MaxMI Subroutine

The MaxMI function invoked in Algorithm 1 is meant to return the highest mutual information attainable using a grid with x columns and y rows on the data D. This is the portion of the procedure that we chose to implement as a heuristic approximation algorithm using dynamic programming.

The Core of ApproxMaxMI: Finding an Optimal x-Axis Partition

The portion of ApproxMaxMI that uses dynamic programming is a function called OptimizeXAxis. Given a fixed y-axis partition, OptimizeXAxis finds the x-axis partition that will lead to a grid with maximal mutual information. Before we describe this function, we first put forth some notational conventions. We will then prove the recursion behind the dynamic programming and present pseudocode for the function.

Preliminaries

We will assume that our set of ordered pairs D is sorted in increasing order by x-value. We denote various partitions of the x-axis by specifying the indices of the endpoints of their columns. Specifically, we will call an ordered list of integers $\langle c_0, \ldots, c_t \rangle$ with $c_0 < c_1 < \ldots < c_t$ an x-axis partition of size t of the $(c_0+1)$-st through $c_t$-th points of D. Given a partition $C = \langle c_0, \ldots, c_t \rangle$ and an integer a with $c_i < a < c_{i+1}$, we let C∪a denote $\langle c_0, \ldots, c_i, a, c_{i+1}, \ldots, c_t \rangle$. If $a = c_i$ for some i, we define C∪a:=C.

Since the dataset D is fixed for our purposes, we will abuse notation in the following way: given an x-axis partition P of m points of D, we let H(P) be the entropy of the distribution induced by those m points on the columns of P. Similarly, H(P,Q) will denote the entropy of the distribution induced by those m points in D on the cells of the grid formed by P and Q where Q is our (fixed) y-axis partition. We will use I(P;Q) analogously. Since Q is fixed just like D, H(Q) will always denote the entropy of the distribution induced by all the points of D on the rows of Q.

Description of the OptimizeXAxis Function

For any discrete random vector (X,Y), a standard definition of I(X;Y) is I(X;Y)=H(X)+H(Y)−H(X,Y) where H(•) denotes Shannon entropy. This means that, using our notation, we have I(P;Q) H(P)+H(Q)−H(P,Q) for all partitions P and Q. However, since Q is fixed, the OptimizeXAxis function need only maximize H(P)−H(P,Q) over all partitions P in order to maximize I(P;Q).

To do so, for a dataset D of size n, begin by fixing a y-axis partition Q. For every m, l∈[n], define F(m,l)=max{H(P)−H(P,Q)} where the maximum is over all partitions of size up to l of the first m points of D. The following recurrence can then be applied for l>1 and 1<m≤n.

$$F(m, l) = \max_{1 \leq i < m}\left\{\frac{i}{m}F(i, l-1) + \frac{m-i}{m}H(\langle i, m \rangle, Q)\right\}$$

This gives rise to a natural dynamic programming algorithm that builds up a table of values of F and eventually returns F(n,l) where l is the desired partition size. The function that carries out this recursion, called OptimizeXAxis, is described in Algorithm 2.

The OptimizeXAxis function restricts itself to drawing x-axis partition lines only between runs of consecutive points that fall in the same row of the y-axis partition Q (called clumps). This increases efficiency without sacrificing optimality because no matter how a clump is split into columns, the contributions of those columns to H(P)−H(P,Q) will be 0. In Algorithm 2, the GetClumpsPartition subroutine is responsible for finding the edges of clumps: it returns the minimal partition that separates every pair of points that lie in distinct clumps.

In Algorithm 2, each $P_{t,l}$ is an optimal partition of size l of the first t clumps of D, and $I_{t,l}$ is defined such that it will contain the corresponding mutual information when t equals the total number of clumps k. The reason OptimizeXAxis returns an array of scores instead of just one is that, since we seek the maximal scores for every possible number of columns, ---
Algorithm 2 OptimizeXAxis(D, Q, x)
---
Require: D is a set of ordered pairs sorted in increasing order by x-value
Require: Q is a y-axis partition of D
Require: x is an integer greater than 1
Ensure: Returns a list of scores ($I_2, \ldots, I_x$) such that each $I_l$ is the maximum value of I(P; Q) over all partitions P of size l.
 1: $\langle c_0, \ldots, c_k \rangle$ ← GetClumpsPartition(D, Q)
 2:
 3: {Find the optimal partitions of size 2}
 4: for t = 2 to k do
 5:   Find s ∈ {1, ..., t} maximizing H($\langle c_s, c_t \rangle$) H($\langle c_s, c_t \rangle$), Q).
 6:   $P_{t,2}$ ← $\langle c_s, c_t \rangle$
 7:   $I_{t,2}$ ← H(Q) + H($P_{t,2}$) − H($P_{t,2}$, Q)
 8: end for
 9:
10: {Inductively build the rest of the table of optimal partitions}
11: for l = 3 to x do
12:   for t = 2 to k do
13:     Find s ∈ {1, ..., t} maximizing $$F(s, t, l) := \frac{c_s}{c_t}(I_{s,l-1} - H(Q)) + \sum_{i=1}^{|Q|} \frac{\#_{i,l}}{c_t}\log\frac{\#_{i,l}}{\#_{*,l}}$$

where $\#_{*,j}$ is the number of points in the j-th column of $P_{s,l-1}$ ∪ $c_t$
and $\#_{i,j}$ is the number of points in the j-th column of $P_{s,l-1}$ ∪ $c_t$ that fall in the i-th row of Q
14:     $P_{t,l}$ ← $P_{s,l-1}$ ∪ $c_t$
15:     $I_{t,l}$ ← H(Q) + H($P_{t,l}$) − H($P_{t,l}$, Q)
16:   end for
17: end for
18: return ($I_{k,2}, \ldots, I_{k,x}$)
--- the entire array is useful. Note that the partitions $P_{t,l}$ appear in our pseudocode for clarity alone; only the scores $I_{t,l}$ are actually used by the function.

Departures from Optimality in the ApproxMaxMI Algorithm

We now describe the two key features that both enable ApproxMaxMI to run in a reasonable amount of time and make it a heuristic approximation.

Equipartitioning One Axis

If, given some number x of columns and some number y of rows, we could run the OptimizeXAxis function on every possible y-axis partition of size y, we would find an optimal grid. But the number of possible y-axis partitions makes this infeasible. Therefore, since the mutual information is bounded from above by the entropy of the less informative axis and the marginal entropies of the axes are maximized by equipartitions (an equipartition is a partition into either rows or columns such that each row/column contains the same number of points), a natural heuristic approach to this problem is to consider only grids for which at least one axis is equipartitioned. To this end, the ApproxMaxMI algorithm fixes an equipartition of size y on the y-axis and then runs OptimizeXAxis. Later, ApproxMaxMI is called again but with the axes switched. The maximum of the two scores obtained is used. Creating the equipartitions involves some tie-breaking when points have identical y-values. This is carried out by the EquipartitionYAxis function, described in Algorithm 3.

Restricting the Number of Clumps

If k is the number of clumps created by a given y-axis partition Q of size y imposed on the dataset D, the runtime of OptimizeXAxis(D,Q,x) is $O(k^2xy)$. This is often too much for large datasets, and so there is one additional parameter to which ApproxMaxMI responds: a maximum number of clumps $\hat{k}$ to allow in its analysis. When $k>\hat{k}$, the true clumps are merged into superclumps in a way that aims to have each superclump contain approximately the same number of points. The algorithm then forgets about the clumps and only considers drawing grid-lines between the super- ---
Algorithm 3 EquipartitionYAxis(D, y)
---

Require: D is a set of n ordered pairs
Require: y is an integer greater than 1
Ensure: Returns a map Q: D → {1, . . . , y} such that Q(p) is the row assignment of the point p and there is approximately the same number of points in each row
1: D ← SortInIncreasingOrderByYValue(D)
2: i ← 1
3: currRow ← 1
4: desiredRowSize ← n/y
5: repeat
6:    S ← {$(a_j, b_j) \in D : b_j = b_i$}
7:    # = |{$(a_j, b_j) \in D : Q(a_j, b_j) = currRow$}|
8:    if # = 0 or |# + S − desiredRowSize| ≤ |# − desiredRowSize| then
9:       Q($(a_j, b_j)$)) ← currRow for every $(a_j, b_j) \in S$
10:      i ← i + |S|
11:      desiredRowSize ← (n − i)/y
12:    else
13:      currRow ← currRow + 1
14:    end if
15: until i > n
16: return Q

--- clumps. The parameter $\hat{k}$ allows for a standard efficiency vs. optimality trade-off. It can be set high enough that $k \leq \hat{k}$ always holds, but the algorithm seems effective even when this condition is not met.

The subroutine that builds the superclumps, called GetSuperclumpsPartition, takes as input only a partition describing the boundaries of the clumps and the parameter $\hat{k}$. It uses the same logic as EquipartitionYAxis (Algorithm 3), only it considers points in the same clump to be a unit rather than points with the same y-value.

The Complete ApproxMaxMI Algorithm

We now give the pseudocode of the ApproxMaxMI algorithm. This is followed by the pseudocode for the ApproxCharacteristicMatrix algorithm, which is slightly different from the outline given in Algorithm 1. This is because, for a fixed number y of rows, OptimizeXAxis returns optimal partitions of size x for every x. Additionally, the Approx-MaxMI algorithm calls the "ApproxOptimizeXAxis" function. This function is identical in every way to OptimizeXAxis (described in Algorithm 2) except that it takes as an argument the maximum number k of superclumps and calls GetSuperclumpsPartition instead of GetClumpsPartition.

---
Algorithm 4 ApproxMaxMI(D, x, y, $\hat{k}$)
---

Require: D is a set of ordered pairs
Require: x, y, and $\hat{k}$ are integers greater than 1
Ensure: Returns a set of mutual information scores $(I_{2,y}, \ldots, I_{x,y})$ such that $I_{i,j}$ is heuristically close to the highest achievable mutual information score using i rows and j columns.
1: Q ← EquipartitionYAxis(D, y)
2: D ← SortInIncreasingOrderByYValue(D)
3: return ApproxOptimizeXAxis(D, Q, x, $\hat{k}$)

---

---
Algorithm 5 ApproxCharacteristicMatrix(D, B, c)
---

Require: D = {$(a_1, b_1), \ldots, (a_n, b_n)$} is a set of ordered pairs
Require: B is an integer greater than 3
Require: c is greater than 0
1: $D^\perp$ ← {$(b_1, a_1), \ldots, (b_n, a_n)$}
2: for all y ∈ {2, . . . , ⌊B/2⌋} do
3:   x ← ⌊B/y⌋
4:   $(I_{2,y}, \ldots, I_{x,y})$ ← ApproxMaxMI(D, x, y, cx)
5:   $(I^\perp_{2,y}, \ldots, I^\perp_{x,y})$ ← ApproxMaxMI($D^\perp$, x, y, cx)
6: end for
7: for (x, y) such that xy ≤ B do
8:   $I_{x,y}$ ← max{$I_{x,y}, I^\perp_{y,x}$}
9:   $M_{x,y}$ ← $I_{x,y}$/min{log x, log y}
10: end for
11: return {$M_{x,y}$ : xy ≤ B}

---

Sample Use Cases

Having described MIC and MINE, we now turn to applying them toward identifying a variety of relationships in a real-world datasets from diverse fields to illustrate their use. The datasets used here are (i) social, economic, health, and political indicators from the World Health Organization (WHO) and its partners; (ii) yeast gene expression profiles from a classic paper reporting genes whose transcript levels vary periodically with the cell cycle; and, (iii) a set of bacterial abundance levels in the human gut microbiota.

The WHO dataset (357 variables, 63,546 variable pairs) is analyze here with MIC, the commonly used Pearson correlation coefficient (ρ), and Kraskovs mutual information estimator (FIG. 7). All three statistics detected many linear relationships. However, mutual information gave low ranks to many non-linear relationships that were highly ranked by MIC (FIG. 7 (a-b)). Two-thirds of the top 150 relationships found by mutual information were strongly linear (|ρ|0.97), whereas most of the top 150 relationships found by MIC had |ρ| below this threshold. Further, although equitability is difficult to assess for general associations, the results on some specific relationships suggest that MIC comes closer than mutual information to this goal (FIG. 7 (i)). Using the non-linearity measure MICρ², we found several interesting relationships (FIG. 7 (e-g)), many of which are confirmed by existing literature. For example, we identified a superposition of two functional associations between female obesity and income per person, one from the Pacific Islands, where female obesity is a sign of status, and one from the rest of the world, where weight and status do not appear to be linked in this way (FIG. 7 (f)).

The yeast gene expression dataset (6,223 genes) was previously analyzed with a special-purpose statistic developed by Spellman et al. to identify genes whose transcript levels oscillate during the cell cycle. Of the genes identified by Spellman et al. and MIC, 70% and 69%, respectively, were also identified in a later study with more time points conducted by Tu et al. However, MIC identified genes at a wider range of frequencies than Spellman et al., and MAS sorted those genes by frequency (FIG. 8). Of the genes identified by MINE as having high frequency (MAS>75th percentile), 80% were identified by Spellman et al., while of the low-frequency genes (MAS<25th percentile) Spellman et al. identified only 20% (FIG. 8 (*b*)). For example, although both methods found the well-known cell-cycle regulator HTB1 (FIG. 8 (*g*)) required for chromatin assembly, only MIC detected the heat-shock protein HSP12 (FIG. 8 (*e*)), which Tu et al. confirmed to be in the top 4% of periodic genes in yeast. HSP12, along with 43% of the genes identified by MINE but not Spellman et al., was also in the top third of statistically significant periodic genes in yeast according to the more sophisticated specialty statistic of Ahdesmaki et al., which was specifically designed for finding periodic relationships without a pre-specified frequency in biological systems.

The analysis of gut microbiota focused on the relationships between prevalence levels of the trillions of bacterial species that colonize the gut of humans and other mammals. The dataset consisted of large-scale sequencing of 16S ribosomal RNA from the distal gut microbiota of mice colonized with a human fecal sample. After successful colonization, a subset of the mice was shifted from a low-fat/plant-polysaccharide-rich (LF/PP) diet to a high-fat/high-sugar 'Western' diet. The initial analysis identified 9,472 significant relationships (out of 22,414,860) between 'species'-level groups called operational taxonomic units (OTUs); significantly more of these relationships occurred between OTUs in the same bacterial family than expected by chance (30% vs. 240.6%).

Examining the 1,001 top-scoring non-linear relationships (MIC-$\rho^2$>0.2), we observed that a common association type was 'non-coexistence': when one species is abundant the other is less abundant than expected by chance, and vice versa (FIG. 9 (*a-b,d*)). Additionally, we found that 312 of the top 500 non-linear relationships were affected by one or more factors for which data were available (host diet, host sex, identity of human donor, collection method, and location in the gastrointestinal tract). Many are non-coexistence relationships that are explained by diet (FIG. 9 (*a*)). These diet-explained non-coexistence relationships occur at a range of taxonomic depths inter-phylum, inter-family, and intra-family and form a highly interconnected network of non-linear relationships (FIG. 9 (*e*)).

The remaining 188 of the 500 highly ranked non-linear relationships were not affected by any of the factors in the dataset, and included many non-coexistence relationships (FIG. 9 (*d*)). These unexplained non-coexistence relationships may suggest inter-species competition and/or additional selective factors that shape gut microbial ecology, and therefore represent promising directions for future study and demonstrate they hypothesis-generating potential of this technology.

Using MIC to Identify Higher-Order Structure in Data

The generality and equitability of MIC enables us not only to rank lists of individual relationships, but also to analyze the higher-order pairwise structure of a dataset by clustering variables according to the strength of their associations without regard to relationship type.

To enable an intuitive and efficient interpretation of how the different variables in a dataset are related to each other, we can generated a network based on MINE output, which we call a spring graph. In a spring graph, the variables in the dataset are represented by nodes, and the relationships between them are represented by edges. The graph is a dynamic physical equilibrium based on a Hookean spring model, which is governed by forces that vary in proportion to either the MIC or the other characteristics of relationships between variables. Thus, every aspect of the spring system between nodes (e.g. spring equilibrium length, spring constants, and coloring) is dependent on one of the properties of the characteristic matrix generated by the MINE approach, allowing the user to examine several of properties of the data simultaneously. To determine the layout of the nodes, numerical integration of these forces is employed until the dynamics converge to one of many potential stable equilibria.

The spring graph is intended to make groups of interrelated variables immediately obvious and therefore easy for the investigator to pick out of a huge initial list of variables and relationships. FIG. 9 (*e*) shows a screenshot of an interactive spring graph generated from the output of the MINE analysis of the gut microbiome dataset described above.

Potential Further Applications

With technology touching almost every aspect of modern life, data about nearly every aspect of our world—from our health to our social activities—is becoming rich and readily available. The MINE family of statistics are a new set of tools designed especially for the rapid exploration of these expanding datasets. These statistics have extremely general applicability, such as, but not limited to, the following several areas:

Medical Data

Medical datasets from large-scale clinical trials, global health organizations, governmental agencies, and insurance companies are becoming larger, more integrated, and more accessible. MINE statistics could be useful for better understanding these datasets, just as it was used to uncover complex relationships in the World Health Organization use case above. This type of analysis, carried out on the other medical datasets mentioned above, could prove extremely fruitful.

Scientific Data

Some scientific fields genomics, proteomics, and the study of the human microbiome, for instance were founded as a result of the explosion of data in the last few decades. Other fields particle physics, sociology, econometrics, neuroscience, earth and atmospheric science predate this development but are also becoming saturated with data. In each of these fields, exploring the emerging large datasets using MINE would be a useful way to see what unknown relationships exist in those datasets. MINE has already been used to analyze both a gene expression dataset and a dataset of bacterial abundance levels from the human microbiome. In the former dataset, MINE identified and characterized hundreds of genes whose expression levels vary periodically with time. In the latter dataset, MINE identified relationships between bacteria in the human microbiome that are entirely novel.

Sports Statistics

Athletic statistics are constantly being generated and mined for relationships. Being able to identify unanticipated relationships could give a team or a analysis group precisely the advantage it requires to beat its competition. MINE was recently used to analyze individual offensive statistics from the 2008 Major League Baseball season. In this analysis, MINE detected offensive statistics that are strongly associated with salary and allowed users to rank teams according to how efficient each teams spending was relative to its offensive performance. Such analyses could be performed with other sports as well.

Financial Data

Everything on Wall Street is measured: trading volume, stock prices, exchange rates, and more are logged at an impressive temporal resolution stretching back decades. Finding hidden patterns in these data is an area of great inquiry, and MINE is well suited for such a task. Using MINE, historical stock price data could be searched to find stocks whose prices are related in interesting ways; the same could be done with exchange rates. Additionally, up-to-the-minute data could be constantly analyzed to find patterns as they emerge in order to inform business decisions.

Internet Connectivity and Usage Data

There is an immense amount of data both in the connectivity structure of the Internet and in our use of internet-based services like Facebook, Twitter, Yelp, search engines, news services, etc. This trove of information has only had its surface scratched. For instance, a recent analysis that combined data from the daily deals website Groupon with user reviews from Yelp threw serious doubt on the accepted wisdom that daily deals are good for a business because they bring it new customers: the analysis found that using Groupon caused a business Yelp rating to fall on average. Analyses like this one could be carried with MINE, leading to the discovery of other surprising relationships in these datasets.

Already, news services like the New York Times use data analysis software to enable their websites to automatically recommend news items to readers based on their demonstrated reading preferences. MINE could aid in this kind of work, aiding researchers to discover new trends in usage habits that could help generate content that is better tailored to the desires of each specific user.

Search engines such as Google also posses massive amounts of data that has not yet been fully leveraged. Google recently demonstrated a potential use of such data: by looking at the frequency of flu-related search queries, the company found it was able to predict flu outbreaks. Moreover, Googles prediction was a few days faster on average than that of the CDC. MINE could be instrumental in guiding such efforts to glean information from search data by helping uncover relationships in large databases of search queries.

Legal and Political Data

More and more data from the legal and political world is being recorded digitally, in forms that make it possible to ask questions about the legal system that were simply not possible to ask previously. The MINE suite of statistics could be use to explore patterns in legal decisions, judge biases, political trends, and congressional and gubernatorial decision making.

Advertising

The advertising world has been revolutionized by the usage of algorithms for view advertising data mathematically first and establish a context for it later. MINE can be used to predict and match advertising to consumers, as well as to analyze its efficacy. MINEs power in this setting stems from the fact that it doesnt need to know anything about the culture and conventions of advertising it just works based on the assumed that more and better data, with better analytical tools, will provide better advertising analytics.

Media Analytics

The age of the Internet and 24-hour news networks has created an overload of news and multimedia. MINE could be used in this arena to track patterns in news, societal memes, or cultural trends. Furthermore, MINE could be applied to processing multimedia by looking for patterns in music and video. For example, companies such as Pandora tag music according to various characteristics in order to personalize music for users. Unfortunately, this tagging is done manually. MINE could be applied to automatically tag characteristics of music or to search for words or common parts in music or video.

Enabling Technologies

In a representative implementation, the subject functionality is implemented in software, as computer program instructions executed by a processor.

More generally, the techniques described herein are provided using a set of one or more computing-related entities (systems, machines, processes, programs, libraries, functions, or the like) that together facilitate or provide the described functionality described above. In a typical implementation, a representative machine on which the software executes comprises commodity hardware, an operating system, an application runtime environment, and a set of applications or processes and associated data, that provide the functionality of a given system or subsystem. As described, the functionality may be implemented in a stand-alone machine, or across a distributed set of machines. The functionality may be provided as a service.

While the above describes a particular order of operations performed by certain embodiments of the invention, it should be understood that such order is exemplary, as alternative embodiments may perform the operations in a different order, combine certain operations, overlap certain operations, or the like. References in the specification to a given embodiment indicate that the embodiment described may include a particular feature, structure, or characteristic, but every embodiment may not necessarily include the particular feature, structure, or characteristic.

While the disclosed subject matter has been described in the context of a method or process, the subject disclosure also relates to apparatus for performing the operations herein. This apparatus may be specially constructed for the required purposes, or it may comprise a general-purpose computer selectively activated or reconfigured by a computer program stored in the computer. Such a computer program may be stored in a computer readable storage medium, such as, but is not limited to, any type of disk including an optical disk, a CD-ROM, and a magnetic-optical disk, a read-only memory (ROM), a random access memory (RAM), a magnetic or optical card, or any type of media suitable for storing electronic instructions, and each coupled to a computer system bus.

While given components of the system have been described separately, one of ordinary skill will appreciate that some of the functions may be combined or shared in given instructions, program sequences, code portions, and the like.

Preferably, the functionality is implemented in an application layer solution, although this is not a limitation, as portions of the identified functions may be built into an operating system or the like.

There is no limitation on the type of computing entity that may implement the client-side or server-side of the connection. Any computing entity (system, machine, device, program, process, utility, or the like) may act as the client or the server.

As described above, one or more functions may be implemented in a cloud-based architecture. As is well-known, cloud computing is a model of service delivery for enabling on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. Available services models that may be leveraged in whole or in part include: Software as a Service (SaaS) (the provider's applications running on cloud infrastructure); Platform as a service (PaaS) (the customer deploys applications that may be created using provider tools onto the cloud infrastructure); Infrastructure as a Service (IaaS) (customer provisions its own processing, storage, networks and other computing resources and can deploy and run operating systems and applications).

The platform may comprise co-located hardware and software resources, or resources that are physically, logically, virtually and/or geographically distinct.

Communication networks used to communicate to and from the platform services may be packet-based, non-packet based, and secure or non-secure, or some combination thereof.

While the disclosed subject matter has been described in the context of a method or process, the subject disclosure also relates to apparatus for performing the operations herein. This apparatus may be specially constructed for the required purposes, or it may comprise a general-purpose computer selectively activated or reconfigured by a computer program stored in the computer. Such a computer program may be stored in a computer readable storage medium, such as, but is not limited to, any type of disk including an optical disk, a CD-ROM, and a magnetic-optical disk, a read-only memory (ROM), a random access memory (RAM), a magnetic or optical card, or any type of media suitable for storing electronic instructions, and each coupled to a computer system bus.

While given components of the system have been described separately, one of ordinary skill will appreciate that some of the functions may be combined or shared in given instructions, program sequences, code portions, and the like.

Having described our invention, what we claim is as follows:

1. A method, comprising:
receiving a dataset;
searching the dataset to identify a pair of variables that have a relationship with one another by:
(a) iteratively evaluating combinations of placements of a fixed number of vertical and horizontal partitions of a two-dimensional scatterplot of the data in the dataset, each combination of vertical (y) and horizontal (x) partitions representing a grid of cells upon which data in the scatterplot induce a probability distribution whose mutual information score can be calculated;
(b) based on the mutual information scores, identifying a grid that results in a highest mutual information score;
(c) repeating steps (a)-(b) for each x-by-y grid resolution up to a maximal grid resolution; and
(d) storing, in a matrix, and for each grid resolution, a normalized highest mutual information score;
generating a network graph based on the matrix, wherein the variables in the dataset are represented in the network graph by nodes, and relationships between nodes are represented by edges; and performing a data analysis on the dataset using the normalized highest mutual information score as represented in the network graph.

2. The method as described in claim 1 wherein the normalized highest mutual information score is generated by normalizing the highest mutual information score achieved by a grid at each grid resolution by $\log \min\{x,y\}$.

3. The method as described in claim 2 further including clustering data using the quantity described as a distance measure.

4. The method as described in claim 1 wherein each probability distribution has marginal entropies, and the normalized highest mutual information score is generated by normalizing the highest mutual information score achieved by a grid at each grid resolution by one of: a minimum of the marginal entropies of the probability distribution induced by that grid, a joint entropy of the probability distribution induced by that grid, an arithmetic mean of the marginal entropies of the probability distribution induced by that grid, and a geometric mean of the marginal entropies of the probability distribution induced by that grid.

5. The method as described in claim 4 further including clustering data using the quantities described as distance measures.

6. The method as described in claim 1 wherein each entry e in the matrix in step (d) is normalized.

7. The method as described in claim 1 wherein, at a given grid resolution, the grid whose induced probability distribution over the data results in the highest mutual information score is such that either all rows or all columns contain just one non-empty cell.

8. The method as described in claim 1 further including identifying a maximum value in the matrix as a maximal information coefficient (MIC).

9. The method as described in claim 8 wherein data in the matrix represents a surface and the MIC corresponds to a highest point on the surface.

10. The method as described in claim 8 further including identifying a difference between the MIC and a linear regression correlation coefficient of the data comprising the relationship to generate a nonlinearity score (NLS) that measures a degree to which a strength of an association is due to a linear correlation.

11. The method as described in claim 8 further including identifying a difference between the MIC and a regression of the data.

12. The method as described in claim 1 further including calculating, given two parameters A and B, a maximum entry of the matrix whose indices (i,j) satisfy $A<ij<B$.

13. The method as described in claim 1 further including identifying a maximum component-wise difference between the matrix and its transpose to generate a measure of a degree of monotonicity of the relationship.

14. The method as described in claim 1 further including identifying a maximum entry in the matrix for a grid with only one vertical or horizontal partition to generate a measure of a degree to which the relationship follows a functional form.

15. The method as described in claim 1 further including calculating $\log(ij)$, where i and j are indices of the matrix described in step (d) that minimize $\log(ij)$, subject to a constraint that a corresponding entry in the matrix is at least a given percent p of a maximal value in the matrix, to generate as a measure of a complexity of the relationship.

16. The method as described in claim 1 further including, given a parameter b, identifying a ratio of two quantities, the first quantity being a maximal entry along a diagonal in the matrix, and a second quantity being an entry at coordinates (b,b) in the matrix.

17. The method as described in claim 1 wherein the matrix is identified by a heuristic approximation algorithm, which comprises:
   (i) drawing a requisite number x of horizontal partitions such that each row delineated by adjacent partitions contains approximately a same number of data points;
   (ii) for each value of L ranging from 2 to the number of data points determined in step (i), identifying the grid with the highest mutual information that contains only left-most points in the scatterplot and uses exactly one vertical partition;
   (iii) for each value of k ranging from 3 to a requisite number y of vertical partitions, and for each value of L ranging from 2 to the number of data points determined in step (i), using the grids identified that have at most k vertical partitions to identify the grid with the highest mutual information that contains only the left-most L points in the scatterplot and uses at most k+1 vertical partitions;
   (iv) swapping the x and y values of the data points; and
   (v) repeating steps (i)-(iii).

18. The method as described in claim 17 further including, following step (i), iterating over data points from left-most to right-most to locate any consecutive sets of points that lie in a same row of the horizontal partitions, each consecutive sets of points being a clump, and in steps (ii) and (iii), allowing vertical partitions to be drawn only between clumps.

19. The method described in claim 18, further including: combining at least some consecutive clumps into a larger grouping until a pre-specified, smaller number of groupings of clumps is obtained; and, in subsequent steps, allowing vertical partitions to be drawn only between groupings of clumps.

20. A computer program product comprising a non-transitory machine-readable medium that stores a program, the program being executed by a machine to detect and use associations in a dataset, comprising:
   code that, for any fixed set D of two-variable data, calculates a function I*(D,x,y) as a maximum mutual information achieved by any grid with x columns and y rows on the data D;
   code that generates a characteristic matrix $M(D)_{x,y}$ of the set D of two-variable data as the function I*(D,x,y) divided by a normalization factor log min{x,y};
   code that generates a maximal information coefficient (MIC) of the set D of two-variable data with sample size n and total grid size less than B(n) as:

$$MIC(D) = \max_{xy<B(n)} M(D)_{x,y};$$

code that generates a network graph based on the characteristic matrix, wherein the two-variable data of the set D are represented in the network graph by nodes, and relationships between nodes are represented by edges; and
   code that performs a data analysis on the dataset using the generated maximal information coefficient (MIC) to identify in the network graph a higher-order pairwise structure of the dataset by clustering variables according to a strength of their associations irrespective of relationship type.

21. Apparatus, comprising:
   a processor;
   computer memory holding a computer program that is executed by the processor to:
   (a) iteratively evaluate combinations of placements of a fixed number of vertical and horizontal partitions of a two-dimensional scatterplot of data in a dataset, each combination of vertical (y) and horizontal (x) partitions representing a grid of cells upon which data in the scatterplot induce a probability distribution whose mutual information score can be calculated;
   (b) based on the mutual information scores, identify a grid that results in a highest mutual information score;
   (c) repeat steps (a)-(b) for each x-by-y grid resolution up to a maximal grid resolution; and
   (d) store, in a data structure, and for each grid resolution, a normalized highest mutual information score;
   (e) generate a network graph based on the data structure, wherein variables in the dataset are represented in the network graph by nodes, and relationships between nodes are represented by edges; and
   performing a data analysis on the dataset using the normalized highest mutual information score, the dataset being one of: sociological data, biological data, medical data, scientific data, sports statistics, financial data, Internet connectivity data, Internet usage data, legal and political data, advertising data and media analytics.

* * * * *